United States Patent [19]

Cochran

[11] Patent Number: 5,068,192

[45] Date of Patent: Nov. 26, 1991

[54] ATTENUATED PSEUDORABIES VIRUS WHICH INCLUDES FOREIGN DNA ENCODING AN AMINO ACID SEQUENCE

[75] Inventors: Mark D. Cochran, La Jolla Calif.

[73] Assignee: Prutech Research and Development Partnership, San Jose, Calif.

[21] Appl. No.: 823,102

[22] Filed: Jan. 27, 1986

[51] Int. Cl.[5] .............. C12N 15/86

[52] U.S. Cl. .............. 435/235.1; 435/172.3; 935/32; 935/65

[58] Field of Search .............. 435/68, 70, 97, 235, 435/290, 243, 172.3, 317

[56] References Cited

U.S. PATENT DOCUMENTS

| | | | |
|---|---|---|---|
| 4,356,270 | 10/1982 | Itakura | 435/317 |
| 4,514,497 | 4/1985 | Kit et al. | 435/235 |
| 4,810,634 | 3/1989 | Post | 435/235 |
| 4,877,737 | 10/1989 | Shih et al. | 435/235.1 |

FOREIGN PATENT DOCUMENTS

| | | |
|---|---|---|
| 0074808 | 3/1983 | European Pat. Off. . |
| 0141458 | 5/1984 | European Pat. Off. . |
| 162783 | 11/1985 | European Pat. Off. . |
| 830293 | 7/1983 | World Int. Prop. O. . |
| 8505122 | 11/1985 | World Int. Prop. O. . |

OTHER PUBLICATIONS

Robbins et al. (1984), *J. Molecular and Appl'd Gen.* vol. 2, pp. 485–496.

Mettenleiter et al. (1985), J. Virology, vol. 56, pp. 307–311.

ZxArnon et al. (1985), *Ann. Inst. Pastexur/Immunol.*, vol. 136D, pp. 271–282.

Post et al. (1981, May), *Cell*, vol. 24, pp. 555–565.

Post et al. (1981, July), *Cell*, vol. 25, pp. 227–232.

Rea et al. (1985), *J. Virology*, vol. 54, pp. 21–29.

C. Mocarski et al. (1980), *Cell*, vol. 22, pp. 243–255.

M. Mackett and G. L. Smith, Proc. Natl. Acad. Sci., U.S.A., vol. 79, 1982, 7415–7419.

D. Panicali and E. Paoletti, Proc. Natl. Acad. Sci. U.S.A., vol. 79, 1982, 4927–4931.

E. Paoletti et al., Proc. Natl. Acad. Sci., U.S.A., vol. 81, 1984, 193–197.

G. L. Smith, M. Macket and B. Moss, Nature, vol. 302, 1983, 490–495.

D. Panicali et al., Proc. Natl. Acad. Sci., U.S.A., vol. 80, 1983, 5364–5368.

G. L. Smith, B. R. Murphy and B. Moss, Proc. Natl. Acad. Sci., U.S.A., vol. 80, 7155–7159.

G. L. Smith et al., Science, vol. 224, 1984, 397–399.

M. Mackett et al., Science, vol. 227, 1985, 433–435.

M. Perkus et al., Science, vol. 229, 1985, 981–984.

*Primary Examiner*—Richard A. Schwartz
*Assistant Examiner*—S. L. Nolan
*Attorney, Agent, or Firm*—John P. White

[57] ABSTRACT

Attenuated pseudorabies viruses are provided which comprise DNA including a sequence essential for replication of the attenuated virus, at least a portion of which is present in a sequence essential for replication of a naturally-occurring pseudorabies virus, and at least one foreign DNA sequence adapted for expression in a host and encoding an amino acid sequence which is antigenic in the host. These viruses are useful as vaccines for immunizing animals against pseudorabies virus disease and other pathogens.

The invention also provides methods of preparing attenuated pseudorabies viruses containing at least one foreign DNA sequence and methods of immunizing animals with vaccines comprised of these viruses.

1 Claim, 13 Drawing Sheets

FIGURE 1
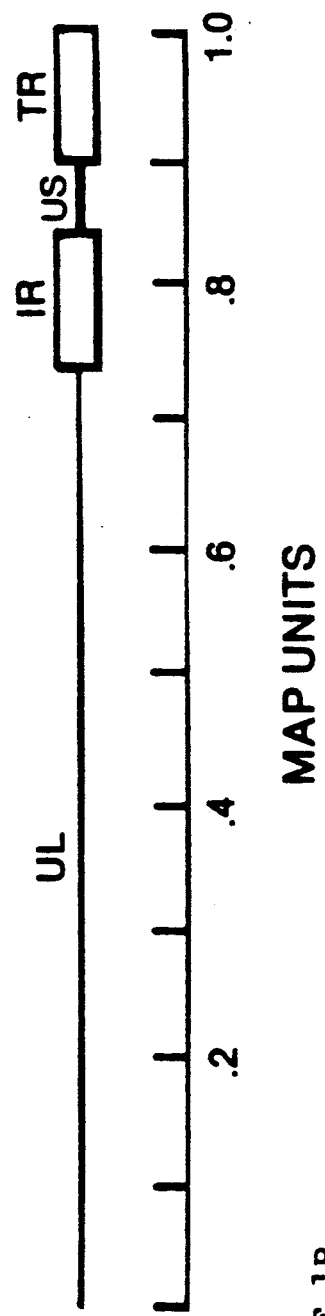
FIGURE 1A.
FIGURE 1B.

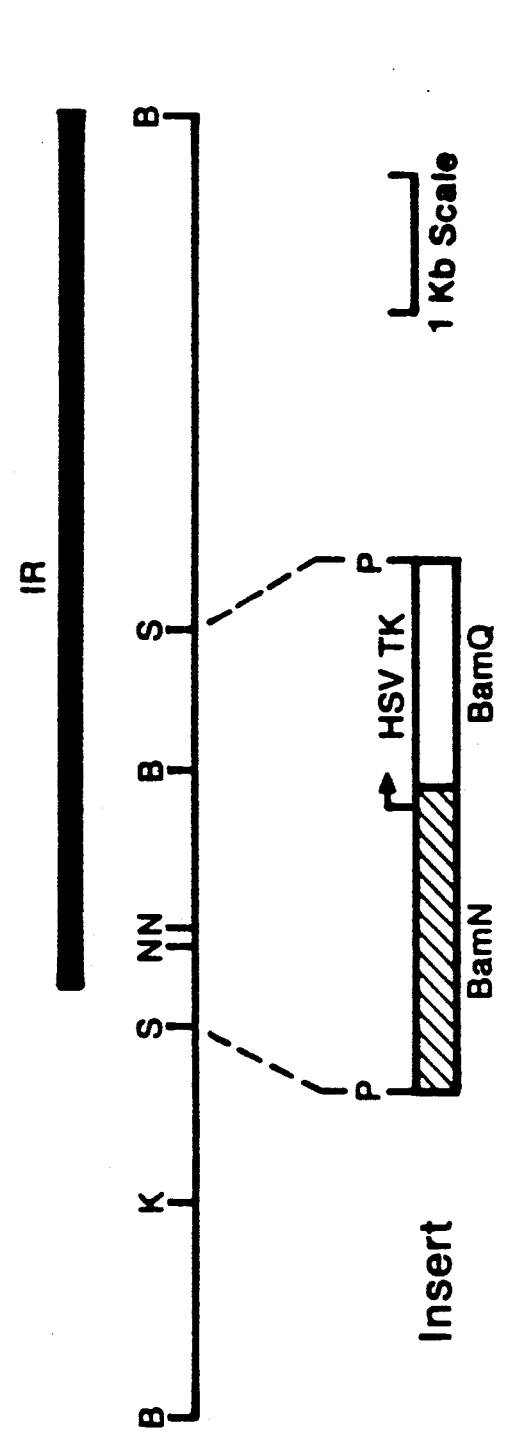
FIGURE 2
FIGURE 2A.
FIGURE 2B.
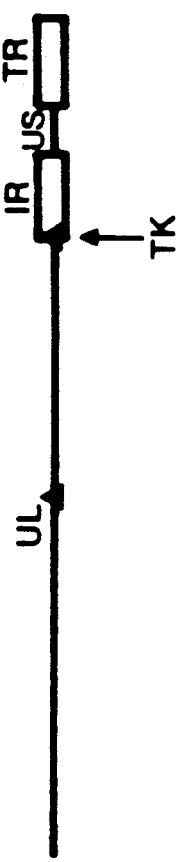
FIGURE 2C.

FIGURE 3
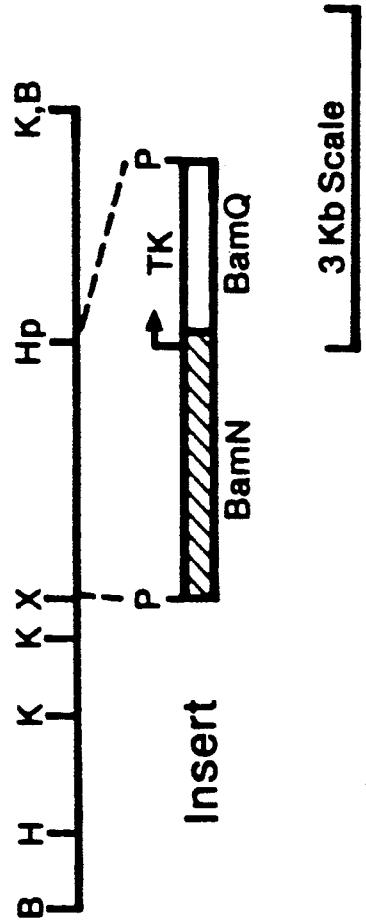
FIGURE 3A.
FIGURE 3B.
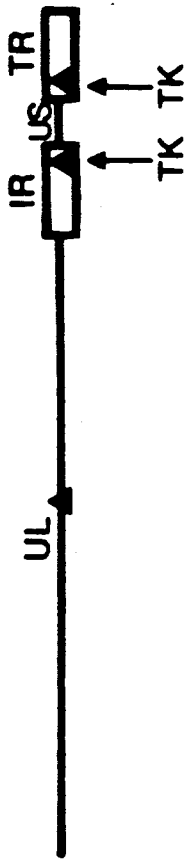
FIGURE 3C.

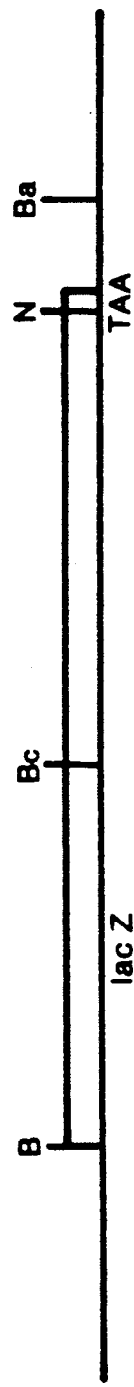
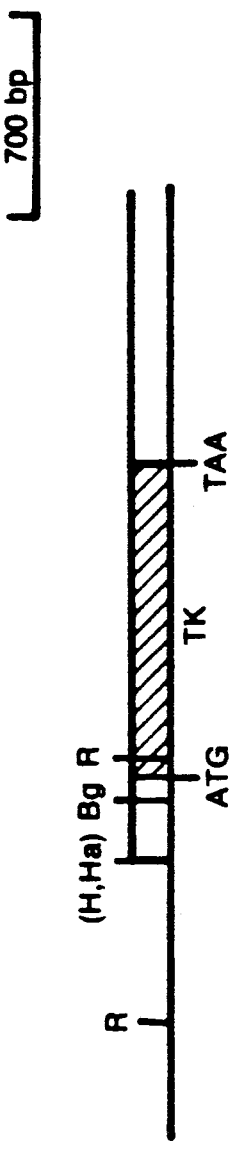
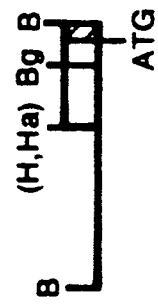
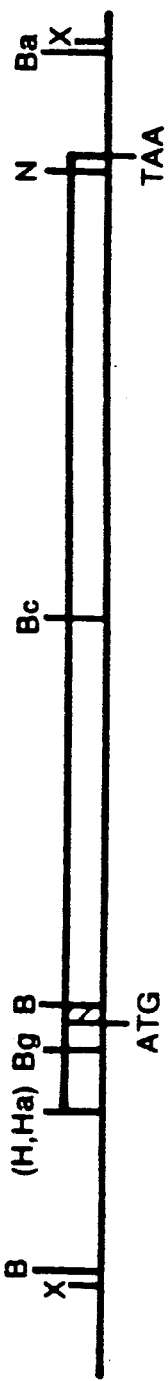
FIGURE 4
FIGURE 4A.
FIGURE 4B.
FIGURE 4C.
FIGURE 4D.

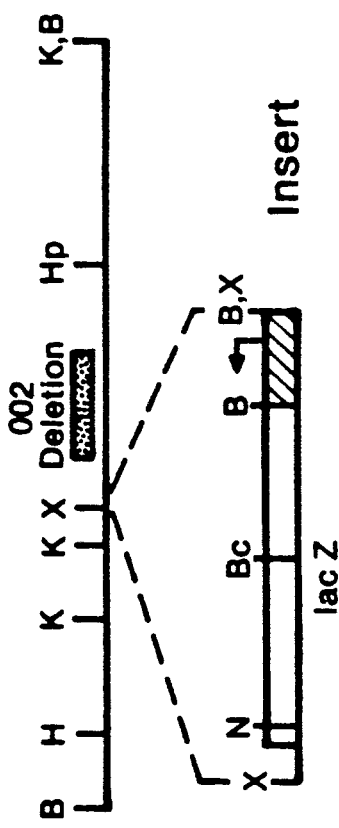
FIGURE 5A.
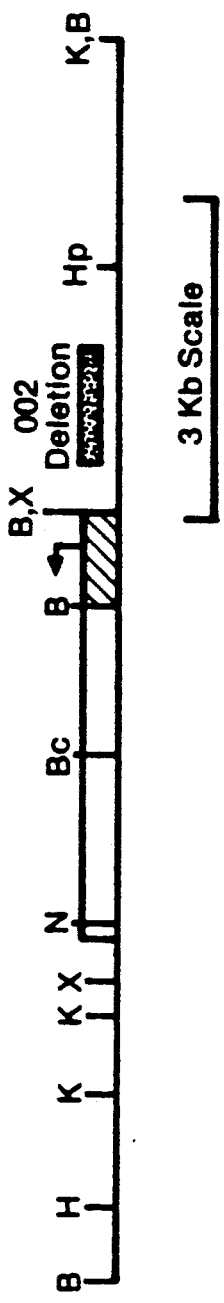
FIGURE 5B.
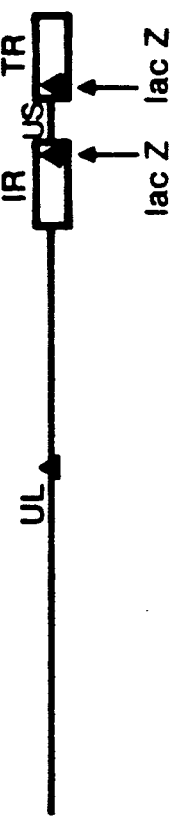
FIGURE 5C.
FIGURE 5

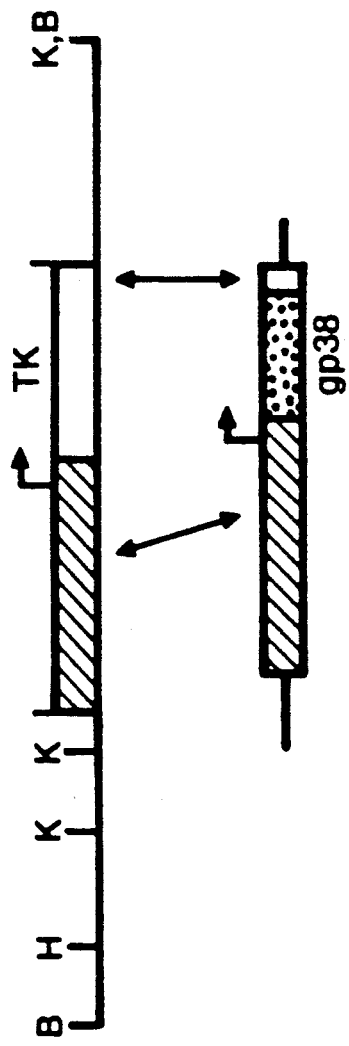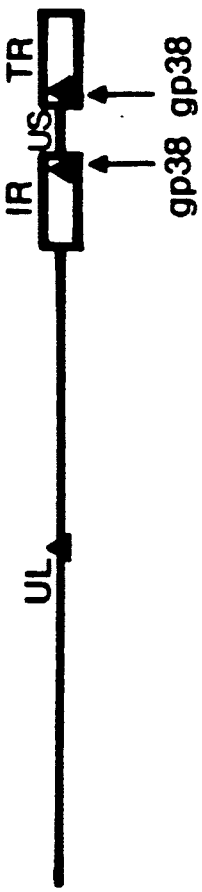
FIGURE 6
FIGURE 6A.
FIGURE 6B.
FIGURE 6C.

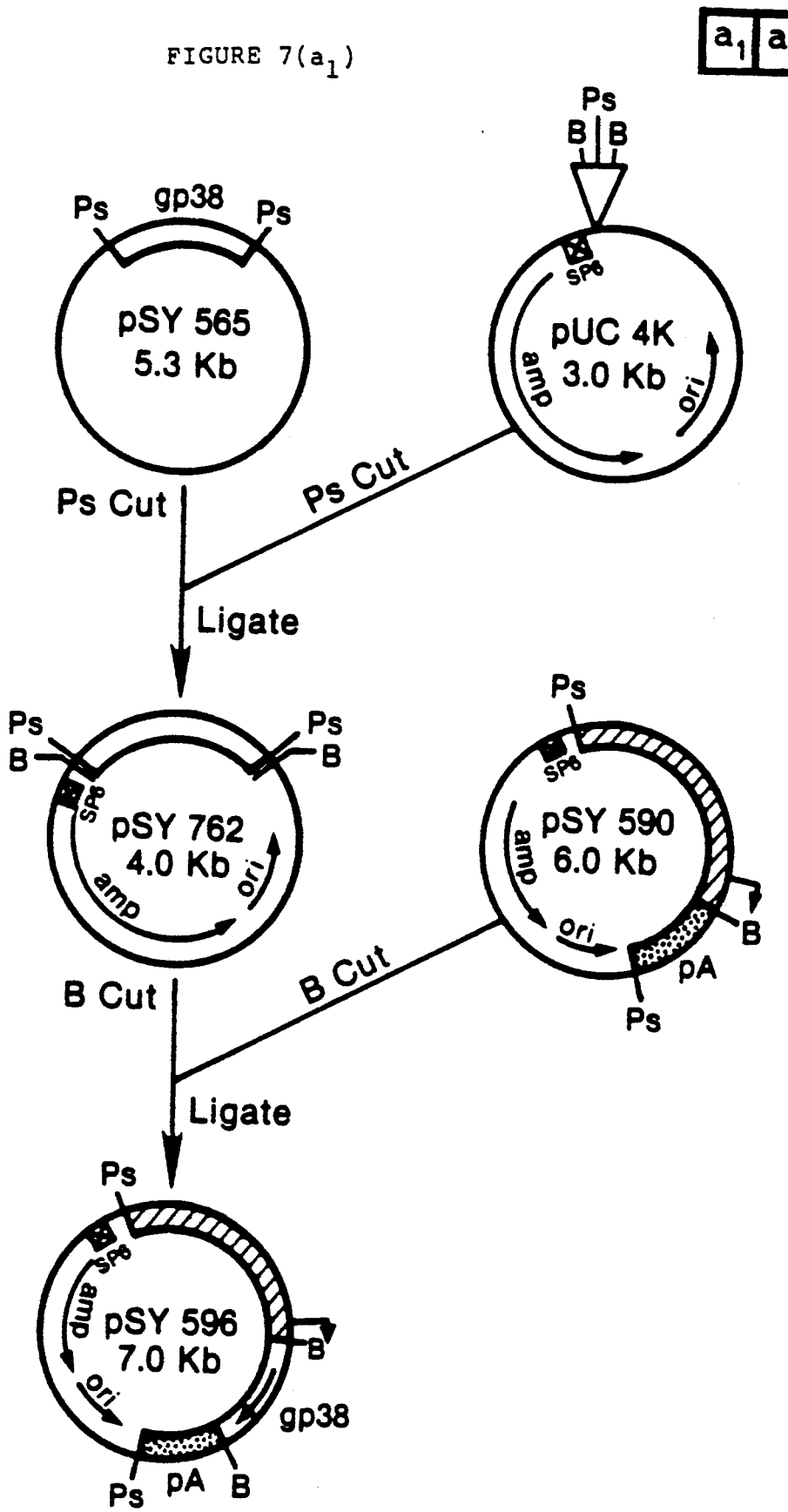
FIGURE 7(a₁)

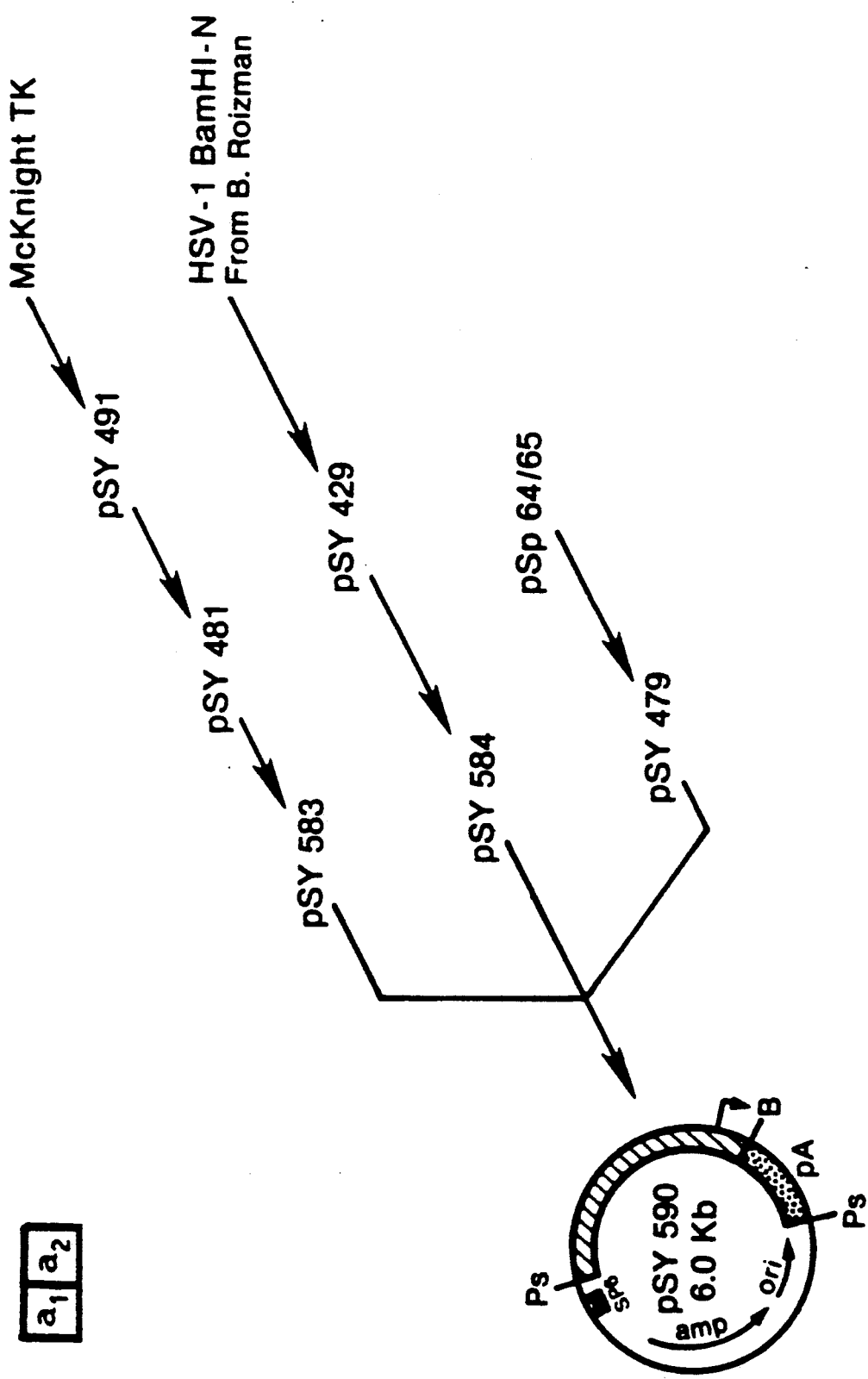
FIGURE 7($a_2$)

FIGURE 8
FIGURE 8A.
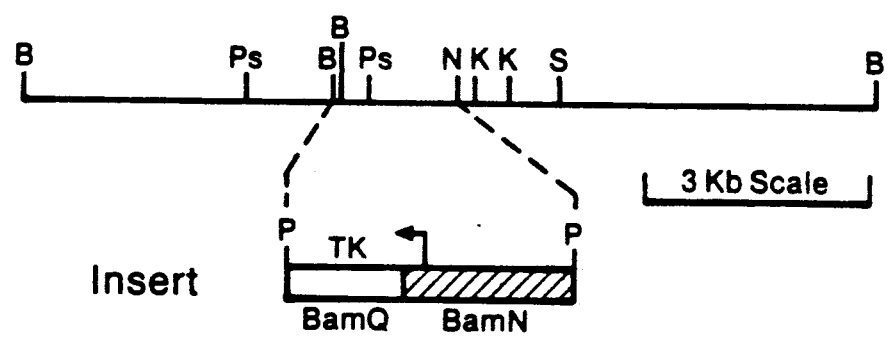
FIGURE 8B.
FIGURE 8C.
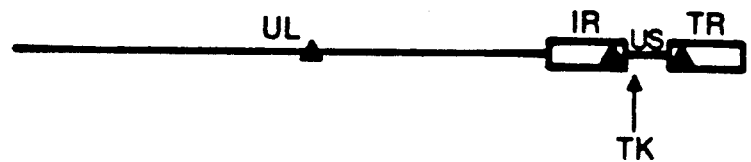

FIGURE 9
FIGURE 9A.
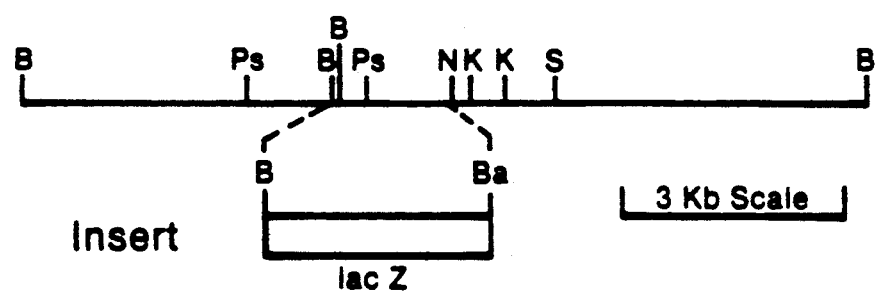
FIGURE 9B.
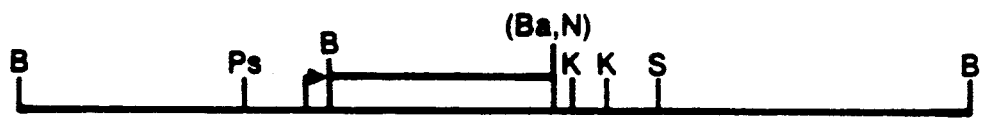
FIGURE 9C.
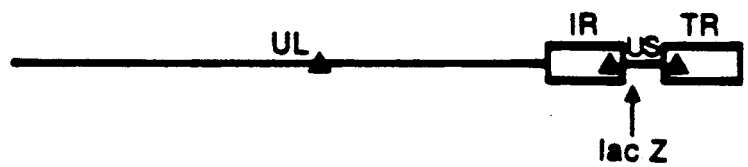

Figure 10B

```
                                                                              RsaI
                                                                              --
435 GCAGAGATATTGCGTCATTTCTGTAGAACCGCAGTTATACTGCACTATAATATTGTACTAATGAAATATGAT   506
    AlaAspIleAlaSerPheSerValGluProGlnLeuTyrCysAspTyrAsnIleValLeuMETLysTyrAsp

EcoRI*
    --

507 GGAAATTACAGTTAGACATGTCTGAATTGGCTGATTAATATTGAATGAATGGCTATGTAATCCAATGAT      578
    GlyAsnLeuGlnLeuAspMETSerGluLeuAlaAspLeuIleLeuAsnGluTrpLeuCysAsnProMETAsp

AluI         EcoRV       RsaI        RsaI
                                 --           --          --          --

579 ATAATGCTATATTATTATCAGCAAACAGATGAAGCTAATAAATGGATATCAATGGTACATCATCATGTACGATT 650
    IleMETLeuTyrTyrTyrGlnGlnThrAspGluAlaAsnLysTrpIleSerMETGlyThrSerCysThrIle

HinfI
                --
                 AvaI    FokI      TaqI                                EcoRI*
                 --      --        --                                  --

651 AAAGTATGTCCTCTAATACGCAGACTCTCGGGATAGGATGTTCGACTACAGACATAAATTCATTTGAAACA    722
    LysValCysProLeuAsnThrGlnThrLeuGlyIleGlyCysSerThrThrAspIleAsnSerPheGluThr

TaqI  HinfI
                                                     --    --

723 GTGGCCAATGCAGAGAAATTAGCTATAACTGATGTTGTCGATGGAGTCAATCATAAATTAGACGTAACAACG   794
    ValAlaAsnAlaGluLysLeuAlaIleThrAspValValAspGlyValAsnHisLysLeuAspValThrThr

AluI
            --                                                          AvaII
                                                                        --
    RsaI RsaI                          AvaII
    -- --                              --

795 AGTACATGTACTATAAGAAATTGTAAAAAACTTGGACCAAGAGAAAATGTCGCTGTAATTCAGTAGGAGGT    866
    SerThrCysThrIleArgAsnCysLysLysLeuGlyProArgGluAsnValAlaValIleGlnValGlyGly
```

Figure 10C

```
                        MboI
                        EcoRI*
                        DpnI
                        BamHI                                              MboII
                                                                           ---
867  CCAAACATACTCGACATAACAGCGGATCCAACAACTGCACCACAAACTGAAAGAATGATGCGTATAAATTGG  938
     ProAsnIleLeuAspIlePheTyrThrAlaAspProThrAlaProGlnThrAlaProGlnThrGluArgMETMETMETArgIleAsnTrp
     TaqI
     ---

RsaI                    MboI
                                                      ---                     ---
939  AAGAGATGGTGGCAAGTCTTTATACAATAGTTGATTATGTCAATCAAATTGTACAAGTCATGTCCAAGCGA  1010
     LysArgTrpTrpGlnValPheTyrThrIleValAspTyrValAsnGlnIleValGlnValMETSerLysArg

DdeI
                 HinfI                              XbaI
                 EcoRI*                             HinfI         DdeI
                 ---                                ---           ---
1011 TCACGGCTCCTTAGATTCTGCTGCCTTTTATTACCGAGTCTAGATATATCTTAGATTAGAATTGTATGATGTGACCT  1086
     SerArgSerLeuAspSerAlaAlaPheTyrTyrArgVal .
     DpnI
     Fnu4HI
     ---
```

ATTENUATED PSEUDORABIES VIRUS WHICH INCLUDES FOREIGN DNA ENCODING AN AMINO ACID SEQUENCE

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

The subject of this invention is a vaccine for pseudorabies virus (herpesvirus suis, suid herpesvirus 1, or Aujesky's disease virus) disease of swine. Swine are the natural host of pseudorabies virus in which infection in older animals is commonly inapparent but may be characterized by fever, convulsions, and death particularly in younger animals. Pseudorabies also infects cattle, sheep, dogs, cats, ferrets, foxes, and rats (1) where the infection usually results in death. Death is usually preceded by intense pruritus, mania, encephalitis, paralysis, and coma. Traditional live vaccines are available for use in swine, but they are lethal for the other animals. An improved vaccine for pseudorabies would induce a more reliable immune response in swine, would be specifically attenuated to be incapable of reversion to virulence, and would not cause disease in other hosts.

In addition to the attributes given above, it would be advantageous to deliver in a single injection with the pseudorabies vaccine other antigens protective against other economically important diseases, for example rotavirus, transmissible gastroenteritis virus, and parvovirus. Such a vaccine would minimize the handling of the animal and the cost of administration. If these antigens were incorporated into the pseudorabies virus as part of the genome of the virus and were designed to be expressed during vaccine virus replication, other advantages would be realized. First, the cost of producing such vaccines would be lowered because the other antigens would be included in the cost of producing a single dose of pseudorabies vaccine. Second, the antigens cloned into pseudorabies virus would be safe —they could never revert to virulence because the majority of the virus nucleic acid sequences are not present in the vaccine. Thirdly, the vaccines would be delivered via a live virus vector that would replicate in living cells in the body which would promote the best possible immune response to give solid protection over the longest time period.

The present invention concerns pseudorabies viruses which have been genetically engineered to contain foreign DNA sequences which encode anitgens which are antigenic in the host animal and may be used to elicit protection against a number of different diseases. These viruses comprise a portion of the pseudorabies virus DNA which is essential for replication of the naturally-occurring virus, but which is missing DNA sequences that are required for full pathogenicity (i.e. they have attenuating deletions). Into these attenuated pseudorabies viruses have been inserted foreign genes under the control of various herpesvirus promoters that direct the expression of foreign antigenic proteins. Vaccines comprised of these viruses are characterized by the efficacy, safety, and economic benefits noted above.

The prior art for this invention stems first from the ability to clone and analyze DNA while in bacterial plasmids. The techniques that are available for the most part are detailed in Maniatis et al. (3112). This publication teaches state of the art general recombinant DNA techniques.

Among the herpesviruses, only two primate herpesviruses (herpes simplex of humans and, to a limited extent, herpes saimiri of monkeys) have been engineered to contain foreign DNA sequences previous to this disclosure. The earliest work on the genetic manipulation of herpes simplex involved the rescue of temperature sensitive mutants of the virus using purified restriction fragments of DNA (3). This work did not involve cloning of the DNA fragments nor the purposeful creation of deletions nor insertions of foreign DNA fragments into the viral genome. The first use of recombinant DNA to manipulate herpes simplex virus involved cloning a piece of DNA from the L-S junction region into the unique long region of the DNA, specifically into the thymidine kinase gene (4). This insert was not a foreign piece of DNA, rather it was a naturally-occurring piece of herpesvirus DNA that was duplicated at another place in the genome. This piece of DNA was not engineered to specifically express any protein, and thus it did not teach how to express protein in herpesviruses. The manipulation of herpes simplex next involved the creation of deletions in the virus genome by a combination of recombinant DNA and thymidine kinase selection. The first step was to make a specific deletion of the thymidine kinase gene (5). The next step involved the insertion of the thymidine kinase gene into the genome at a specific site, and then the thymidine kinase gene and the flanking DNA at the new site were deleted by a selection against thymidine kinase (6). In this manner herpes simplex alpha-22 gene has been deleted (6). In the most recent refinement of this technique, a 15,000 bp sequence of DNA has been deleted from the internal repeat of herpes simplex virus (7).

The insertion of genes that encode protein into primate herpesviruses have involved seven cases: the insertion of herpes simplex glycoprotein C back into a naturally occurring deletion mutant of this gene in herpes simplex virus (8); the insertion of glycoprotein D of herpes simplex type 2 into herpes simplex type 1 (9), again with no manipulation of promoters since the gene is not really 'foreign'; the insertion of hepatitis B surface antigen into herpes simplex virus under the control of the herpes simplex ICP4 promoter (10); and the insertion of bovine growth hormone into herpes saimiri virus with an SV40 promoter that in fact didn't work in that system (an endogenous upstream promoter served to transcribe the gene) (11). Two additional cases of foreign genes (chicken ovalbumin gene and Epstein-Barr virus nuclear antigen) have been inserted into herpes simplex virus (18), and glycoprotein X of pseudorabies virus has been inserted into herpes simplex virus (20).

These limited cases of deletion and insertion of genes into primate herpesviruses demonstrate that it is possible to genetically engineer primate herpesvirus genomes by recombinant DNA techniques. The methods that have been used to insert genes involve homologous recombination between the viral DNA cloned on plasmids and purified viral DNA transfected into the same animal cell. In aggregate this is referred to as the homologous recombination technique. This technique has been adapted with some modifications to allow us to engineer pseudorabies virus. Several key elements of the genetic engineering of pseudorabies are not made obvious from these previous primate herpesvirus studies. The present invention demonstrates where to make deletions that serve to attenuate pseudorabies virus, where to make the insertions of the foreign genes to get them stably contained within the pseudorabies virus genome, and which promoters are effective in expressing foreign proteins in the pseudorabies virus genome.

Pseudorabies virus is classified as an alphaherpesvirus with a class D genome structure (12); that is, it contains two copies of a single repeat region, one located between the unique long and unique short DNA region and one at the terminus of the unique short region (see FIG. 1). Herpes simplex virus is an alphaherpesvirus with a class E genome (12); that is , it contains two copies of each of two repeats. Herpes saimiri is a gammaherpesvirus with a class B genome: that is, it contains numerous reiterations of the same sequence at both termini (12). As the genome structure differs significantly between these different classes of herpesviruses, and because the different viruses attack different cells within their hosts and elicit different pathologies, it is necessary in each instance to establish which specific regions can be removed in order to attenuate and which regions can be altered to express foreign genes.

Pseudorabies virus has been studied using the tools of molecular biology including the use of recombinant DNA techniques. BamHI, KpnI, and BglII restriction maps of the virus genome have been published (13, 14). DNA transfection procedures have been utilized to rescue temperature sensitive and deletion mutants of the virus by the homologous recombination procedure (13). There are two examples of deletions that have been made in the pseudorabies virus genome —one is a thymidine kinase gene deletion (15, 19) disclosed in U.S. Pat. No. 4,514,497 entitled "Modified Live Pseudorabies Viruses". This patent describes a method to delete the thymidine kinase gene of pseudorabies virus to produce a virus with reduced virulence for mice and teaches thymidine kinase deletions only, but does not suggest other attenuating deletions, nor does it suggest insertion of foreign DNA sequences. The other example involves the deletion of a small DNA sequence around a HindIII restriction site in the repeat region (16). From this work a patent application has been filed in Europe that involves other larger deletions in the unique short region as well. Published on May 15, 1985, European Patent Publication No. 0141458, based upon European Patent Application No. 84202474.8, filed on Oct. 12, 1984, entitled "Deletion Mutant of a Herpesvirus and Vaccine Containing Same", describes deletions in the unique short region of pseudorabies virus and their attenuating effect.

The present invention concerns deletions which have been introduced into the pseudorabies genome at sites previously undisclosed. These deletions are shown to be attenuating and to increase the utility of the virus as a vector for the expression of foreign genes as a vaccine. Foreign DNA sequences have been introduced into the attenuated pseudorabies virus and expressed as proteins. One embodiment of the invention concerns a vaccine useful for preventing pseudorabies and other swine diseases with a single inoculum.

Other relevant pseudorabies literature concerns the presence of naturally-occurring deletions in the genome of two vaccine strains of pseudorabies viruses (14, 17). These deletions are responsible, at least in part, for the attenuated nature of these vaccines. Such naturally-occurring deletions do not teach the methods for making these deletions starting with wild type pseudorabies virus DNA, nor do they suggest other locations at which to make attenuating deletions. Our deletions do not occur at the sites of these natural deletions, nor do they overlap these deletions in any way. Thus the presence of these naturally occurring deletions is simply a curious phenomenon that does not teach or instruct the current invention. There are no examples of naturally-occurring insertions of foreign DNA in herpesviruses.

SUMMARY OF THE INVENTION

Attenuated pseudorabies viruses are provided which are comprised of DNA including a sequence essential for replication of the attenuated virus, at least a portion of which is present in a sequence essential for replication of a naturally-occurring pseudorabies virus, and at least one foreign DNA sequence adapted for expression in a host and encoding an amino acid sequence which is antigenic in the host.

Vaccines comprised of an effective immunizing amount of a virus of this invention and a suitable carrier are useful for immunizing animals against pseudorabies virus disease. Multivalent vaccines, also comprised of an immunizing amount of a virus of this invention and a suitable carrier are useful for immunizing animals against pseudorabies virus disease and at least one other pathogen.

The invention also provides methods of preparing attenuated pseudorabies viruses including at least one foreign DNA sequence and methods of immunizing animals with vaccines comprised of these viruses.

The invention further provides an isolated nucleic acid molecule which encodes swine rotavirus glycoprotein 38.

BRIEF DESCRIPTION OF THE FIGURES

FIG. 1 —Details of wild type Shope strain PRV.

Figure 10A:
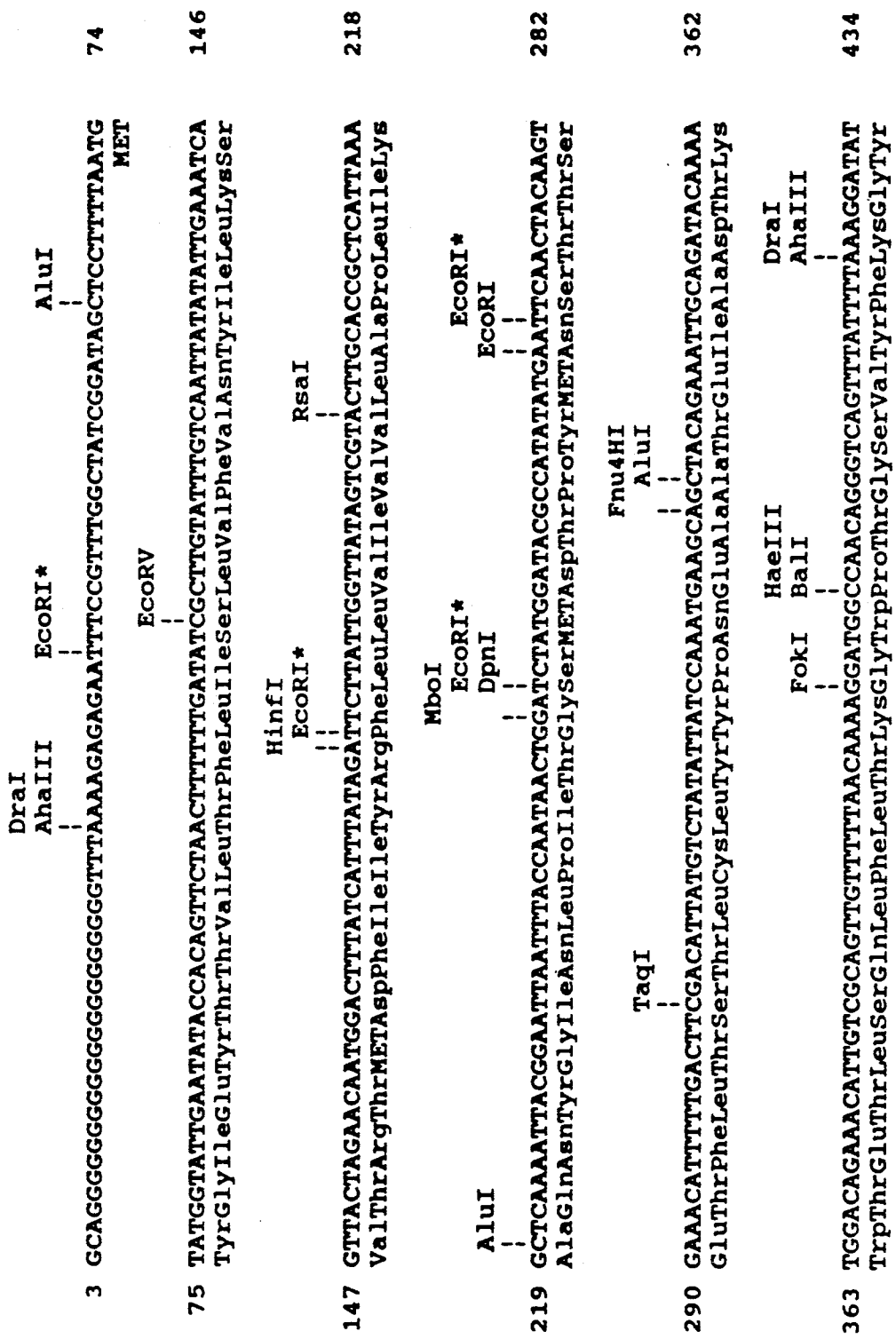

A. Diagram of PRV genomic DNA showing the unique long region (UL), the unique short region (US), the internal repeat region (IR), and the terminal repeat region (TR).

B. BamHI restriction enzyme map of PRV. Fragments are numbered in order of decreasing size.

FIG. 2 —Details of S-PRV-004 Construction and Map Data.

A. Detailed map of BamHI #8' and #8. The location of the internal repeat (IR) region is shown.

B. Detailed map of BamHI #8'-TK-8 fragment ultimately present in the recombinant virus.

C. Diagram of the S-PRV-004 DNA genome showing the location of the HSV-1 TK gene inserted into the junction region between the UL and IR regions.

Restriction Enzyme Legend: B =BamHI; K =KpnI; N =NdeI; P =PvuII; S =StuI.

FIG. 3 Details of S-PRV005 Construction And Map Data.

A. Detailed map of BamHI #5. The HSV-1 TK gene fused to the HSV-1 ICP4 promoter is shown on a PvuII fragment.

B. Detailed Map of BamHI #5 after the insertion of the TK gene construct.

C. Diagram of the S-PRV-005 DNA genome showing the location of the TK gene inserted into both copies of BamHI #5 in the repeat region of the genome and the creation of new deletions.

Restriction Enzyme Legend: B =BamHI; H =HindIII; Hp =HpaI; K =KpnI; P =PvuII; X =XbaI.

FIG. 4 —Construction of the Foreign DNA Insert Used In S-PRV-010.

A. Diagram of the relevant portion of pJF751 that contains the lac Z (β-galactosidase) gene. The position of the TAA termination codon for the polypeptide is indicated.

B. Diagram of the promoter sequence from the HSV-1 TK gene.

C. Diagram of the RsaI fragment of the TK gene now with BamHI modified ends.

D. Diagram of the final plasmid that contained the lac Z gene fused to the HSV-1 TK promoter.

Restriction Enzyme Legend: Ba =BamHI; Ba =BalI; Bc =BclI; Bg =BglII; H =HindIII; Ha =HaeIII; N =NdeI; R =RsaI; X =XbaI.

FIG. 5 —Details of S-PRV-010 Construction And Map Data.

A. Detailed map of BamHI #5. The lac Z gene (β-galactosidase) fused to the HSV-1 TK promoter is shown on an XbaI fragment (see FIG. 4). The position of the deletion in S-PRV-002 is shown.

B. Detailed map of BamHI #5 after the insertion of the lac Z gene construct.

C. Diagram of the S-PRV-010 genome DNA showing the location of the lac Z gene inserted into both copies of BamHI #5 in the repeat region of the genome.

Restriction Enzyme Legend: B BamHI; Bc =BclI; H =HindIII; Hp =HpaI; K KpnI; N =NdeI; X =XbaI.

FIG. 6 —Details of S-PRV-007 Construction and Map Data.

A. Detailed map of BamHI #5 from S-PRV-005.

B. Detailed map of BamHI #5 after the substitution of the TK gene with the swine rotavirus gp38 gene.

C. Diagram of the S-PRV-007 DNA genome showing the location of the gp38 gene inserted into both copies of BamHI #5 in the repeat regions of the genome.

Restriction Enzyme Legend: B =BamHI; H =HindIII; K =KpnI.

FIG. 7(a and a2) —Construction of the Foreign DNA Insert Used in S-PRV-007.

FIG. 8 —Details of S-PRV-012 Construction And Map Data.

A. Detailed map of PRV extending from BamHI #10 through BamHI #7.

B. Detailed map of PRV extending from BamHI #10 through BamHI #7 after the insertion of the TK gene into the recombinant virus.

C. Diagram of the S-PRV-012 DNA genome showing the location of the TK gene inserted into the gpX region and the creation of a deletion that removes most of the coding region of the gpX gene and renders the virus unable to synthesize the gpX polypeptide.

Restriction Enzyme Legend: B =BamHI; K =KpnI; N =NdeI; P =PvuII; Ps =PstI; S =StuI.

FIG. 9 —Details of S-PRV-013 Construction and Map Data.

A. Detailed map of PRV extending from BamHI #10 through BamHI #7.

B. Detailed map of PRV extending from BamHI #10 through BamHI #7 after the insertion of the lac Z gene into the recombinant virus.

C. Diagram of the S-PRV-013 DNA genome showing the location of the lac Z gene inserted into the gpX region and the creation of a deletion that removed most of the coding region of the gpX gene and rendered the virus unable to synthesize the gpX polypeptide.

Restriction Enzyme Legend: B =BamHI; Ba =BalI; K =KpnI; N =NdeI; Ps =PstI; S =StuI.

FIGS. 10 ( A,B and C) —Swine rotavirus gp38 gene sequence in pSY565.

DETAILED DESCRIPTION OF THE INVENTION

The present invention concerns an attenuated pseudorabies virus comprising DNA which includes a sequence essential for replication of the attenuated virus, at least a portion of which is essential for replication of a naturally-occurring pseudorabies virus, and at least one foreign DNA sequence adapted for expression in a host and encoding an amino acid sequence which is antigenic in the host. In one embodiment of the invention the amino acid sequence encoded by the foreign DNA sequence is expressed in the host, such expression resulting in the production of antibodies directed to the amino acid sequence, and such antibodies conferring protection on the host against subsequent infection by a pathogen other than pseudorabie virus.

The DNA sequence which is essential for replication of the attenuated virus may be synthetic or it may be derived from a naturally-occurring pseudorabies virus. The amino acid sequence encoded by the foreign DNA sequence may be a polypeptide. In one embodiment of the invention, the polypeptide is a protein. Furthermore, the foreign DNA sequence may be adapted for expression by an endogenous upstream pseudorabies virus promoter or by an inserted upstream promoter from pseudorabies virus or from a species of herpesvirus other than pseudorabies virus.

The pseudorabies virus may be attenuated as a result of a deletion in the DNA of at least a portion of a repeat sequence. Additionally, a sequence not located within a repeat may also be deleted. This sequence may be at least a portion of a gene. In one embodiment of the invention, the deleted sequence not located within a repeat is at least a portion of the gene encoding thymidine kinase.

The deletion of at least a portion of a repeat sequence may include a portion of a unique sequence, e.g. the junction region of the internal repeat and the unique long sequence. Furthermore, the foreign DNA sequence may be inserted where the deletion has occurred. In a preferred embodiment of the invention the virus has a deletion in the gene encoding pseudorabies thymidine kinase, the deletion of at least a portion of a repeat sequence comprises a portion of the junction region of the internal repeat and the unique long sequence and the foreign DNA sequence is inserted where the deletion in the junction region occurred. In a specific embodiment the foreign DNA sequence is adapted for expression by the herpes simplex type I ICP4 gene promoter and encodes herpes simplex virus type I thymidine kinase. This virus is designated S-PRV-004.

The invention concerns attenuated pseudorabies viruses with a deletion in a nonessential sequence of both repeat sequences. The insertion of the foreign DNA sequence may occur in a nonessential sequence of the virus and can occur in a nonessential sequence in both repeat sequences. In a preferred embodiment of the invention the virus has a deletion in the gene encoding pseudorabies thymidine kinase, a nonessential sequence in both repeat sequences is deleted and the foreign DNA sequence is inserted in a nonessential sequence in both repeats. In a specific embodiment, the foreign DNA sequence is adapted for expression by the herpes simplex type I ICP4 gene promoter and encodes herpes simplex virus type I thymidine kinase. This virus is designated S-PRV-005 and has been deposited with the American Type Culture Collection (ATCC) Rockville, MD under Accession No. VR 2109. In another specific embodiment of the invention the foreign DNA sequence is adapted for expression by the herpes simplex type I ICP4 gene promoter and encodes swine rotavirus glycoprotein 38. This virus is designated S-PRV-007 and is deposited under ATCC Accession No. VR 2118. In a further specific embodiment, the foreign DNA is adapted for expression by the herpes simplex type I thymidine kinase gene promoter and encodes E. coli beta-galactosidase (lacZ gene). This virus is designated S-PRV-010 and has been deposited under ATCC Accession No. VR 2110.

The invention also provides attenuated pseudorabies viruses with a deletion in a portion of a sequence not located within a repeat sequence.

Vaccines useful for immunizing an animal against pseudorabies virus disease are also provided. These vaccines comprise an effective immunizing amount of the attenuated pseudorabies viruses of this invention and a suitable carrier, e.g. a physiologically balanced culture medium which contains stabilizing agents.

The invention further concerns multivalent vaccines useful for immunizing an animal against pseudorabies virus disease and at least one other pathogen. The host animal is immunized against other pathogens by the production within the animal of foreign antigens encoded by the foreign DNA sequence of the attenuated pseudorabies virus. Animals may be immunized against pseudorabies virus and other pathogens by administering to them a suitable dose of a vaccine of this invention. Such animals include swine, dogs, cats, sheep or bovine animals. The vaccine may be administered by intramuscular, subcutaneous, intraperitoneal or intravenous injection. The vaccine may also be administered intranasally or orally.

The invention also provides methods of preparing attenuated pseudorabies viruses which include a foreign DNA sequence. One method involves isolating naturally-occurring pseudorabies viral DNA and using restriction enzyme digestion to produce DNA restriction fragments. These restriction fragments are purified by agarose gel electrophoresis to obtain specific DNA fragments which are treated with appropriate enzymes, known to those skilled in the art, to produce modified viral DNA fragments These modified viral DNA fragments are capable of binding to bacterial plasmid DNA sequences. Suitable bacterial plasmids are separately treated with appropriate restriction enzymes, known to those skilled in the art, to produce bacterial plasmid DNA sequences capable of binding to modified viral DNA fragments. These bacterial plasmid DNA sequences are then combined with the modified viral DNA fragments under suitable conditions to allow the viral DNA to bind to the bacterial DNA and form a viral-bacterial plasmid.

The viral-bacterial DNA plasmid is then mapped by restriction enzymes to generate a restriction map of the viral DNA insert. The viral-bacterial DNA plasmid is then treated with restriction enzymes known in the art to cut the viral DNA sequence of the viral-bacterial DNA plasmid. Foreign DNA is separately digested with appropriate restrictive enzymes to produce foreign DNA restriction fragments. Fragments including desired genes are mixed with the viral-bacterial DNA plasmid sequences under suitable conditions to allow the formation of a viral-bacterial-foreign DNA plasmid. This plasmid, containing the foreign DNA sequence, is transfected with naturally-occurring intact pseudorabies viruses into animal cells. The animal cells are maintained under suitable conditions to allow the naturally-occurring pseudorabies viral DNA to regenerate the naturally-occurring virus and a small percentage of viruses which have recombined with the foreign DNA sequence of the plasmid. Some of these recombined viruses have deletions in their genome as a result of deletions in the viral DNA insert of the plasmid. Viruses including the foreign DNA sequence are identified and subsequently plaque purified away from the wild type virus.

The foreign DNA sequence incorporated into the pseudorabies viral genome may encode herpes simplex type I thymidine kinase, E. coli beta-galactosidase or swine rotavirus glycoprotein 38.

Another method of preparing attenuated pseudorabies viruses which include a foreign DNA sequence is provided. This direct ligation method involves isolating and digesting pseudorabies viral DNA with appropriate restriction enzymes to produce viral DNA restriction fragments. Foreign DNA is separately digested with restriction enzymes to produce foreign DNA restriction fragments. The viral DNA restriction fragments are reacted under suitable conditions to allow the formation of viral-foreign DNA fragments.

Animal cells are then transfected with the viral-foreign DNA fragments and maintained under suitable conditions to allow the viral-foreign DNA fragments to regenerate pseudorabies viruses. Viruses which include desired foreign DNA sequences are identified and plaque purified away from the other viruses.

In one embodiment of the invention, the direct ligation method involves incorporating into the pseudorabies viral genome a foreign DNA sequence encoding E. coli beta-galactosidase.

The invention further provides methods of preparing vaccines comprised of pseudorabies viruses which include a foreign DNA sequence. These methods include cultivating the virus in roller bottles or in a suspension of microcarrier beads. The vaccines can also be prepared by cultivating the virus by batch fermentation.

The invention also provides an isolated nucleic acid molecule having the nucleic acid sequence set forth in FIG. 10 and encoding swine rotavirus glycoprotein 38. This nucleic acid molecule may be a cDNA molecule. The invention further concerns a mRNA molecule which is complementary to the nucleic acid molecule set forth in FIG. 10.

A bacterial recombinant cloning vehicle which comprises plasmid DNA and the cDNA of this invention is also provided. In a specific embodiment of the invention, the plasmid DNA comprises pBR322 DNA. This cloning vehicle is designated pSY565. A bacterial host cell which comprises this cloning vehicle is additionally provided. In a specific embodiment, the host cell is an E. coli. cell designated DH-1/pSY565 deposited under ATCC Accession No. 53,340.

MATERIALS AND METHODS

PREPARATION OF PSEUDORABIES VIRUS (PRV) STOCK SAMPLES. Pseudorabies virus (PRV) stock samples were prepared by infecting Vero cells at a multiplicity of infection of 0.01 PFU/cell in Dulbecco's Modified Eagle Medium (DMEM) containing 2 mM glutamine, 100 units/ml penicillin, 100 units/ml streptomycin (these components were obtained from Irvine Scientific or equivalent supplier, and hereafter are referred to as complete DME medium) plus 1% fetal bovine serum. After cytopathic effect was complete, the medium and cells were harvested and the cells were pelleted at 3000 rpm for 5 minutes in a desk top centrifuge. The cells were resuspended in 1/10 the original volume of medium, and an equal volume of 2 times autoclaved skim milk (9% skim milk powder in $H_2O$ wgt/vol) was added. The virus sample was frozen and thawed 2 times, aliquoted, and stored frozen at 31 70° C. The titer was usually about $10^8$ plaque forming units per ml.

PREPARATION OF PRV DNA. For PRV DNA preparation, a confluent monolayer of Vero cells in a 25 $cm^2$ flask or a 60 mm petri dish was infected with 100 $\mu l$ of virus sample in 1 ml medium. Adsorption proceeded for 1-2 hours at 37° C. in a humidified incubator with 5% $CO_2$ in air. After adsorption, 4 ml of complete DME medium plus 1% fetal bovine serum was added. After overnight incubation, or when the cells were showing 100% cytopathic effect, the cells were scraped into the medium with a cell scraper (Costar brand). The cells and medium were centrifuged at 3000 rpm for 5 minutes in a clinical centrifuge. The medium was decanted, and the cell pellet was gently resuspended in 0.5 ml solution containing 0.01 M Tris pH 7.5, 1 mM EDTA, and 0.5% Nonidet P-40 (NP40, an ionic detergent comprising an octyl phenol ethylene oxide condensate containing an average of 9 moles ethylene oxide per molecule, purchased from Sigma Chemical Co., St. Louis, MO.). The sample was incubated at room temperature for 10 minutes. Ten $\mu l$ of a stock solution of RNase A (Sigma) was added (stock was 10 mg/ml, boiled for 10 minutes to inactive DNAase). The sample was centrifuged for 5 minutes at 3000 rpm in a clinical centrifuge to pellet nuclei. The DNA pellet was removed with a pasteur pipette or wooden stick and discarded. The supernatant was decanted into a 1.5 ml Eppendorf tube containing 25 $\mu l$ of 20% sodium dodecyl sulfate (Sigma) and 25 $\mu l$ proteinase-K (10 mg/ml; Boehringer Mannheim supplier). The sample was mixed and incubated at 37° C. for 30-60 minutes. An equal volume of water-saturated phenol was added and the sample was mixed on a vortex mixer for 5 minutes. The sample was centrifuged in an Eppendorf minifuge for 5 minutes at full speed. The upper aqueous phase was removed to a new Eppendorf tube, and two volumes of −20° C. absolute ethanol were added and the tube put at −20° C. for 30 minutes to precipitate nucleic acid. The sample was centrifuged in an Eppendorf centrifuge in the cold room for 5 minutes. The supernatant was decanted, and the pellet was washed one time with cold 80% ethanol. The pellet was dried in a lyophilizer, and rehydrated in 17 $\mu l$ $H_2O$. For the preparation of larger amounts of DNA, the procedure was scaled up to start with a 800 $cm^2$ roller bottle of Vero cells. The DNA was stored in $H_2O$ or in 0.01M Tris pH 7.5, 1 mM EDTA at −20° C.

PHENOL EXTRACTION. Phenol extraction was performed on any convenient volume of DNA sample, typically between 100 $\mu l$ to 1 ml. The DNA sample was diluted in 0.1M Tris pH 7.5, 1 mM EDTA and an equal volume of water saturated phenol was added. The sample was vortexed briefly and placed on ice for 3 minutes. After centrifugation for 3 minutes in a microfuge, the aqueous layer was removed to a new tube and was precipitated by ethanol.

ETHANOL PRECIPITATION. DNA in a sample was concentrated by ethanol precipitation. To the DNA sample were added 1/10 volume of 3M sodium acetate pH 7.5 and 3 volumes of cold ethanol. The DNA was precipitated for 30 minutes at −70° C. or overnight at −20° C. and then pelleted by centrifugation in the microfuge for 15 minutes at 4° C. The pellet was washed once with 200 1 of cold 80% ethanol and pelleted again for 10 minutes at 4° C. After air drying or lyophilization, the pellets were resuspended in the appropriate buffer or $H_2O$.

RESTRICTION ENZYME DIGESTION. DNA was cut by restriction enzymes using the buffer recommended by the manufacturer (International Biotechnologies Inc., New Haven, CT. (IBI), Bethesda Research Laboratories, Betheada, MD. (BRL), and New England Biolabs, Beverly, MA). Whenever possible, the concentration of DNA was kept below 1 $\mu g/50$ $\mu l$. Incubation was at 37° C. for 1-4 hours.

AGAROSE GEL ELECTROPHORESIS OF DNA. To visualize the restriction pattern of the DNA, 5 $\mu l$ of loading buffer (5X electrophoresis buffer, 0.01% bromphenol blue dye, 50 mM EDTA, and 50% glycerol) was added. The samples were loaded into a lane in a horizontal submarine electrophoresis unit containing a 0.6% agarose gel. The electrophoresis buffer was 40 mM Tris, 10 mM EDTA, adjusted to ph 7.8 with acetic acid, and with or without 0.5 $\mu g/ml$ ethidium bromide. The gel was run at 40-14 50V for 18 hours, and the gel was removed and stained with 0.5 $\mu g/ml$ ethidium bromide for 30 minutes. The DNA bands were visualized on a long wavelength UV transilluminator.

PHOSPHATASE TREATMENT OF DNA. Phosphatase treatment of DNA was performed by adding 1 $\mu l$ (25 units) of calf intestinal phosphatase (Boeringer Mannheim) directly to the restriction enzyme digestion reactions and continuing the incubation for 30 minutes at 37° C. The phosphatase was inactivated for 60 minutes at 65° C. prior to phenol extraction.

POLYMERASE FILL-IN REACTION. DNA was resuspended in buffer containing 50 mM Tris pH 7.4, 50 mM KCl, 5 mM $MgCl_2$, and 400 $\mu M$ each of the four deoxynucleotides. Ten units of Klenow DNA polymerase (BRL) was added and the reaction was allowed to proceed for 15 minutes at room temperature. The DNA was then phenol extracted and ethanol precipitated as above.

EXONUCLEASE RESECTION REACTION. DNA was resuspended in 100 $\mu l$ of 60 mM Tris pH 8.0, 0.66 mM $MgCl_2$, 1 mM betamercapthoethanol. The sample was warmed to 30° C. for 5 minutes, and 10 units of lambda exonuclease III (BRL) was added. At frequent time intervals (e.g. every 2.5 minutes), 10 $\mu l$ aliquots were diluted into 100 $\mu l$ of 30 mM sodium acetate pH 4.5, 250 mM NaCl, 1 mM $ZnSO_4$, 4 $\mu g/100$ $\mu l$ yeast tRNA, 30 units/ 100 $\mu l$ S1 nuclease. After 45 minutes at 30° C., 15 $\mu l$ of stop buffer consisting of 625 mM Tris pH 9.0, 150 mM EDTA, 1% SDS was added. The samples were then phenol extracted and ethanol precipitated as above. The DNA digestion products were then analyzed and purified by agarose gel electrophoresis.

PHENOL EXTRACTION OF DNA FROM AGAROSE. DNA bands cut from low melting point agarose gels were diluted to less than 0.5% agarose to a final concentration of 0.3 M sodium acetate. The samples was heated to 65° C. to melt the agarose and then cooled to 37° C. for 5 minutes. An equal volume of phenol was added and the sample was phenol extracted three times (see PHENOL EXTRACTION). The DNA was then ethanol precipitated and the pellet resuspended at a concentration of 3-6 fmole DNA/μl.

LIGATION. DNA was joined together by the action of the enzyme T4 DNA ligase (BRL). Ligation reactions contained 10 fmoles DNA, 20 mM Tris pH 7.5, 10 mM MgCl$_2$, 10 mM dithiothreitol (DTT), 200 μM ATP, and 20 units T4 DNA ligase in 10 μl final reaction volume. The ligation was allowed to proceed for 3-16 hours at 15° C. Typically DNA fragments to be ligated together were added at an equal molar ratio. Typically two different DNA fragments were joined during ligation, but joining of three or four different DNAs at once was also possible.

RESTRICTION MAPPING OF DNA. Restriction mapping of DNA was performed as detailed in Maniatis et al. (2). Once it was cloned, the DNA was digested with a number of different restriction enzymes and the DNAs were analyzed on agarose gels and the sizes of the resulting fragments were measured. A double digest with two different restriction enzymes was performed on the same DNA sample to aid in the interpretation of the maps. Another approach used was to cut the DNA with a restriction enzyme that has a single unique site in the DNA, label the end of the DNA with $^{32}$P using T4 DNA kinase or Klenow DNA polymerase (see POLYMERASE FILL-IN REACTION) and then cut the DNA with other restriction enzymes at low temperature or for short times so that only partial digestion occurred. The subsequent analysis of the partial digestion fragments on agarose gels served to order the restriction sites on the map. All of these mapping procedures are well understood by those skilled in the art and are detailed in Maniatis et al. (2). The most complete restriction maps can only be composed once the DNA has been sequenced, and the sequence is then analyzed by a computer searching for all the known restriction enzyme sites. Some of our maps have been generated from sequence information.

SOUTHERN BLOTTING OF DNA. The general procedure for Southern blotting was taken from Maniatis et al. (2). DNA was blotted to nitrocellulose filters (S&S BA85) in 20 X SSC (1 X SSC =0.15M NaCl, 0.015M sodium citrate pH 7.0), and prehybridized in hybridization solution consisting of 30% formamide, 1 X Denhardt's solution (0.02% polyvinylpyrrolidone (PVP), 0.02% bovine serum albumin (BSA), 0.02% Ficoll), 6 X SSC, 50 mM NaH$_2$PO$_4$ pH 6.8, 200 μg/ml salmon sperm DNA for 4-24 hours at 55° C. Labeled probe DNA was added that had been labelled by nick translation using a kit from Bethesda Research Laboratories (BRL) and one $^{32}$P-labeled nucleotide. The probe DNA was separated from the unincorporated nucleotides by NACS column (BRL) or on a Sephadex G50 column (Pharmacia). After overnight hybridization at 55° C., the filter was washed once with 2 X SSC at room temperature followed by two washes with 0.1 X SSC, 0.1% sodium dodecyl sulfate (SDS) for 30 minutes at 55° C. The filter was dried and autoradiographed.

DNA TRANSFECTION FOR GENERATING RECOMBINANT VIRUS. The method is based upon the calcium phosphate DNA precipitation procedure of Graham and Van der Eb (21) with the following modifications. For transfection into animal cells, 0.1-0.2 μg of plasmid DNA containing the foreign homovector) was mixed with 0.3 μg of intact DNA. Both DNAs were stored either in H$_2$O or 0.01 M Tris pH 7.5, 1 mM EDTA and the final volume should be less than 0.25 ml. To the mixture was added an equal volume of 2×HEPES buffered saline (10g N-2-hydroxyethyl piperazine N'-2-ethanesulfonic acid (HEPES), 16g NaCl, 0.74g KCl, 0.25g Na$_2$HPO$_4$.2H$_2$O, 2g dextrose per liter H$_2$O and buffered with NaOH to pH 7.4). The mixture was then diluted to 0.5 ml by the addition of the appropriate volume of 1×HEPES buffered saline (prepared by diluting the above solution 1:1 with H$_2$O). After mixing, 35 μl of 2.2 M CaCl$_2$ was added to the DNA mixture and mixed. The mixture was incubated at room temperature for 30 minutes. Medium was removed from an 80% confluent monolayer of rabbit skin cells or Vero cells growing in a 25 cm$^2$ flask, and the DNA mixture was added to the flask and distributed over the cells. After a 30 minute incubation at room temperature, 5 mls of complete DME medium plus 10% fetal bovine serum was added. The cells were incubated for 5 hours at 37° C. in a humidified incubator containing 5% CO$_2$ in air. The medium was changed at 5 hours either with or without a glycerol shock. When used, the glycerol shock consisted of removing the medium and adding DME containing 20% glycerol for 3 minutes at room temperature, followed by a wash with 10% glycerol in DME, and a wash in 5% glycerol in DME, followed by the addition of fresh complete DME medium plus 10% fetal bovine serum. The cells were incubated at 37° C. as above for 3-4 days until cytopathic effect from the virus was 50-100%. Virus was harvested as described above for the preparation of virus stocks, and this stock was referred to as a transfection stock and it was subsequently screened for recombinant virus either with or without a selection mechanism to enrich for recombinant plaques as described below.

DIRECT LIGATION PROCEDURE FOR GENERATING RECOMBINANT PRV. Rather than using homovectors and relying upon homologous recombination to generate recombinant virus, we have also developed the technique of direct ligation to insert foreign genes into PRV. In this instance, the cloned foreign gene did not require flanking PRV DNA sequences but only required that it have restriction sites available to cut out the foreign gene fragment from the plasmid vector. A compatible restriction enzyme was used to cut PRV DNA. A requirement of the technique was that the restriction enzyme used to cut the PRV DNA must cut at a limited number of sites. We have used XbaI, which cut PRV DNA in two places, and contemplate the use of HindIII (2 cuts), EcoRV (2 or 3 cuts), or NdeI (3-5 cuts). The PRV DNA was mixed with a 30-fold molar excess of plasmid DNA, and the mixture was cut with the appropriate restriction enzyme. The DNA mixture was phenol extracted and ethanol precipitated to remove restriction enzymes, and ligated together according to the ligation procedure detailed above. The ligated DNA mixture was then phenol extracted, ethanol precipitated, and resuspended in 298 μl 0.01M Tris pH 7.5, 1 mM EDTA. Forty-two μl of 2M CaCl$_2$ was added, followed by an equal volume of 1×HEPES buffered saline (see above), and the sample was used to transfect animal cells as described above.

The virus in the transfection stock was then screened for foreign DNA inserts as described below. The advantage of the direct ligation technique was that it required less construction of sub-clones in the plasmid state, and that the recombinant virus were present in the transfection stock at a much higher frequency than with homologous recombination.

HAT SELECTION OF RECOMBINANT PRV EXPRESSING THYMIDINE KINASE. Deletion mutants of PRV which suffered deletions in the thymidine kinase (TK) gene were constructed. These PRV strains have been designated S-PRV-002 and S-PRV-003 and have been deposited with the ATCC under Accession No. VR 2107 and VR 2108 respectively. These TK minus (TK-) viruses have been used as recipients for the insertion of the foreign herpes simplex type 1 (HSV-1) TK gene. One HSV-1 TK gene that we have used contains the HSV-1 ICP4 promoter and was from B. Roizman (5). It was sub-cloned to lie between two flanking regions of PRV DNA, for example by insertion of the TK gene into PRV BamHI #5 fragment between XbaI and HpaI sites. The plasmid construct was then transfected with the PRV TK- DNA to yield recombinant virus. The transfection stock was enriched for TK-containing virus by the HAT selection procedure of Campione-Piccardo et al. (22). The transfection stock was used to infect monolayers of 143 TK- cells in 60 mm culture dishes that had been preincubated in HAT medium for 16 hours at 37° C. (HAT medium: medium 199 containing 2 mM glutamine, 100 units/ml penicillin, 100 units/ml streptomycin, 10% fetal bovine serum, $5 \times 10^{-5}$ M hypoxanthine, $10^{-5}$ M thymidine, $5 \times 10^{-6}$ M aminopterin). Samples of the transfection stock virus were infected into the 143 TK- cells using 3 to 7 log dilutions of virus. After one or two days at 37° C., the dishes inoculated with the highest dilution of virus and still showing virus plaques were harvested for virus stocks, and the selection was repeated a second time. The virus stock harvested from the second HAT selection was used in a plaque assay and individual plaques were picked and tested for foreign DNA inserts as described below.

BROMODEOXYURIDINE SELECTION OF RECOMBINANT PRV. In order to insert a foreign gene in place of a TK gene already present in the PRV genome, the foreign gene was cloned in plasmids so that it contained the same flanking homology regions as the TK genes. These flanking regions could be part of the TK gene itself, or parts of PRV that flank the TK gene. In either case, the plasmid DNA containing the foreign gene was transfected with intact PRV genomic DNA containing the HSV-1 TK gene. The transfection stock of recombinant virus was grown for two selections in 143 TK- cells in the presence of 40 µg/ml bromodeoxyuridine (BUDR, Sigma) in complete DME medium plus 10% fetal bovine serum. The drug BUDR is an analogue of thymidine that is recognized by the viral enzyme thymidine kinase (TK) and is ultimately incorporated into DNA. When incorporated into the DNA, BUDR is mutagenic and lethal and thus selects against viruses that have an active TK gene. By this selection method, viruses that had exchanged their TK gene for a foreign gene by homologous recombination were enriched in the population. Screening for the recombinant viruses was then performed by one of the techniques detailed below.

HYBRIDIZATION SCREEN FOR RECOMBINANT PRV. One procedure used is described by Villarreal and Berg (23). The technique involved doing a plaque assay on PRV under agarose, removing the agarose once plaques had formed, and lifting the cell monolayer from the dish onto a nitrocellulose membrane filter. The filter was then processed through the Southern procedure for DNA hybridization as detailed above. The DNA probe used in the procedure was made from the foreign gene that had been inserted into the virus. Thus plaques that contain the foreign gene were identified, and they were picked from the agarose overlay that had been saved.

BLUOGAL SCREEN FOR RECOMBINANT PRV. When the foreign gene encoded the enzyme β-galactosidase, the the plaques that contained the gene were visualized more easily. The chemical Bluogal TM (BRL) was incorporated at the level of 200–300 µg/ml into the agarose overlay of the plaque assay, and the plaques that expressed active β-galactosidase turned blue. The blue plaques were then picked and purified by further blue plaque isolations. Other foreign genes were inserted by homologous recombination such that they replaced the β-galactosidase gene; in this instance non-blue plaques were picked for purification of the recombinant virus.

ANTIBODY SCREEN FOR RECOMBINANT PRV. A third method for screening the recombinant virus stock was to look directly for the expression of the foreign gene with antibodies. PRV plaques were spotted and picked by inserting a toothpick through the agarose above the plaque and scraping the plaque area on the dish. Virus was then rinsed from the toothpick by inserting it into a well of a 96-well microtiter dish (Falcon Plastics) containing a confluent monolayer of Vero cells that had been washed 3 times in DME medium without serum. It was important for the virus to grow without serum at this stage to allow for the immunological procedure to work. After cytopathic effect was complete, the plates were put at −70° C. to freeze and lyse the cells. The medium was thawed, and the freeze/-thaw procedure was repeated a second time. Then 50–100 µl of medium was removed from each well and filtered under vacuum in a DotBlot TM apparatus (BRL) through a nitrocellulose membrane (S&S BA85). The filter blots were soaked in a blocking solution of 0.01 M Tris pH 7.5, 0.1 M NaCl, 3% bovine serum albumin at room temperature for two hours with shaking. The filter blots were then removed to a sealable bag (Sears Seal-A-Meal or equivalent), and 10 mls of the blocking solution that contained 10 µl of antibody specific for the foreign protein was added. After overnight incubation at room temperature with shaking, the blot was washed 3 times with 100 mls 0.01 M Tris pH 7.5, 0.1 M NaCl, 0.05% Tween 20 detergent (Sigma). The blot was put in another sealable bag and 10 mls blocking solution containing $10^6$ counts per minute of $^{125}$I-protein A (New England Nuclear) was added. After allowing the protein A to bind to the antibody for 2 hours at room temperature with shaking, the blot was washed as above, dried, and overlayed with an x-ray film and an intensifying screen (Dupont) and autoradiographed for 1-3 days at −70° C. The film was developed by standard procedures, and the positive wells which contained the recombinant virus were further purified.

METHOD FOR cDNA CLONING SWINE ROTAVIRUS gp38 GENE Virus Growth. The OSU strain of procine rotavirus (ATCC-VR-892) was propagated on MA-104 cells (Resus monkey kidney cells from MA Bioproducts). Confluent monolayers were infected at the multiplicity of infection of greater than 10 in DMEM containing 5 μg/ml trypsin. Cells were incubated with virus for 48 hours or until a cytopathic effect was obtained. Media and cell debris were collected and centrifuged at 10,000 ×g for 20 minutes at 4° C. The supernatant containing the rotavirus was then centrifuged at 10,000 ×g in a preparative Beckman Ti45 rotor at 4° C. Virus pellets were resuspended in SM medium (50 mM Tris-HCl pH 7.5, 100 mM KCL, 10 mM $MgCl_2$) and homogenized lightly in a Douncetype homogenizer. The resuspended virus was centrifuged at 100,000 ×g for 10 minutes then loaded onto 25-50% CsCl gradients in SM buffer. Gradients were centrifuged at 100,000 ×g for 4 hours at 20° C. The two blue-white bands representing intact virions and cores of rotavirus were collected, diluted, and the CsCl gradient procedure was repeated a second time. Virus obtained from the second gradient was dialyzed overnight against SM buffer at 4° C.

Viral RNA Isolation. Dialyzed rotavirus was twice extracted with an equal volume of SDS/phenol then twice more with chloroform: isoamylalcohol (24:1). The double stranded RNA was precipitated with ethanol in the presence of 0.2 M sodium acetate, centrifuged and resuspended in water. The yield was typically 100 μg from 1,000 $cm^2$ of infected cells.

Synthesis and Cloning of gp38 cDNA, 160 μg of doublestranded rotavirus RNA obtained from the above procedure was mixed with one μg each of two synthetic oligo nucleotide primers in a volume of 160 μl (sequences of primers were:

5'-GGGAATTCTGCAGGTCACATCATACAATTCTAATCTAAG-3' and

5'-GGGAATTCTGCAGGCTTTAAAAGAGAGAATTTCCGTTTGGCTA-3')

derived from the published sequence of bovine rotavirus (24). The RNA-primer mixture was boiled for 3 minutes in a water bath then chilled on ice. Additions of 25 μl of 1 M Tris-HCl pH 8.3, 35 μl of 1 M KCl, 10 μl of 0.25 M $MgCl_2$, 7 μl of 0.7 M 2-mercaptoethanol, 7 μl of 20 mM dNTP's, and 6 μl of reverse transcriptase (100 units) were made sequentially. The reaction was incubated at 42° C. for 1.5 hours then 10 μl of 0.5 M EDTA pH 8.0 was added and the solution was extracted once with chloroform: phenol (1:1). The aqueous layer was removed and to it 250 μl of 4 M ammonium acetate and 1.0 ml of 95% ethanol was added, the mixture was frozen in dry ice and centrifuged in the cold. The resulting pellet was resuspended in 100 μl of 10 mM Tris-HCl pH 7.5 and the ammonium acetate precipitation procedure was repeated. The pellet was resuspended in 100 μl of 0.3 M KOH and incubated at room temperature overnight then at 37° C. for 2 hours. The solution was brought to neutral pH by addition of 10 μl of 3.0 M HCl and 25 μl of 1.0 M Tris-HCl pH 7.5. The resulting single-stranded cDNA was then precipitated two times by the above described ammonium acetate-ethanol procedure. The pellet obtained was resuspended in 50 μl of 10 mM Tris-HCl pH 7.5, 100 mM NaCl, 1 mM EDTA, boiled in a water bath for 2 minutes then incubated at 59° C. for 16 hours. The solution was lyophilized to a volume of 15 μl and the resulting double-stranded cDNA was run on a 1.0% agarose gel (Sigma agarose Type II). The ethidium bromide stained DNA migrating a 1,000-1,100 base pair length was excised from the gel and electroeluted in a CBS electroeluter device. The solution was lyophilized, and the cDNA was resuspended in 25 μl of water. To this solution was added 2 μl of 1.0 M Tris-HCl pH 7.5, 2 μl of 1 M KCl, 1 μl of 0.25 M $MgCl_2$, 1 μl of 20 mM dNTP's, and 5 units of *E. coli* DNA polymerase I. The reaction was incubated at room temperature for 15 minutes, then chloroform/- phenol extracted and ammonium acetate-ethanol precipitated as described above. The resulting cDNA was tailed with dCTP using terminal deoxynucleotide transferase (BRL buffer and enzyme used). The reaction was stopped with 2 μl of 0.5 M EDTA, chloroform/phenol extracted and precipitated with sodium acetate in the presence of 10 μl of carrier tRNA. The resuspended cDNA was mixed with 200 ng of dGMP-tailed Pst I cut pBR322 (BRL catalog #5355SA) in 200 μl of 10 mM Tris-HCl pH 7.5, 100 mM NaCl, 1 mM EDTA, heated to 65° C. for 5 minutes then 57° C. for 2 hours. The annealed cDNA-vector pBR322 was transformed onto *E. coli* DH-1 cells prepared for high efficiency transformation. Colonies that showed sensitivity to ampicillin and tetracycline resistance were grown and DNA was prepared and cut with Pst I to determine the size of the cDNA insert. Several clones having Pst I inserts of 1,050-1,100 base pairs were analyzed and found to have identical restriction enzyme digest patterns. The largest clone was designated pSY565 and have been deposited with the ATCC under accession number 53,340. For one of these clones, the 1,100 base pair Pst I insert was subcloned into a M13 phage sequencing vector. The entire DNA sequence of this clone was determined and is shown in FIG. 10. The location of the gp38 open reading frame was determined from the amino acid homology to human and bovine sequences already published (24).

EXAMPLES

EXAMPLE 1

S-PRV-004

We have created a virus that has a deletion in the junction region between the unique long DNA and the internal repeat of PRV, and a deletion in the endogenous PRV thymidine kinase gene in the unique long region. Into the junction deletion we have cloned the herpes simplex type 1 (HSV-1) thymidine kinase (TK) gene under the control of the ICP4 promoter. This virus is designated S-PRV-004.

To create this virus, we first cloned the SalI #1 fragment of PRV. PRV DNA was prepared and then cut with SalI restriction enzyme. The cut DNA was electrophoresed on an agarose gel and the largest SalI band (15 kb) was purified from the gel (see PHENOL EXTRACTION OF DNA FROM AGAROSE). The purified DNA was ligated into the plasmid pSP64 (see LIGATION) and the DNA mixture was used to transform *E. coli* HB101 according to Maniatis et al. (2). The SalI #1 clone was mapped for restriction sites.

The homologous recombination procedure was used to create S-PRV-004 (see FIG. 2). The exact position of the junction region was determined by sequencing the DNA from SalI #1 fragment. It was found that hte junction region was positioned between two StuI sites (FIG. 2A). Two fragments of DNA from the SalI clone were used to create the homology vector for recombination. One was a fragment from BamHI #8'from StuI to BamHI and the other was from BamHI #8'from BamHI to StuI (see FIGS. 1B and 2A). These fragments were cloned into the BamHI site of pSP64. This plasmid was cut with StuI, and a 3.8 kb PvuII fragment, obtained from B. Roizman (5), The University of Chicago, and containing the ICP4 promoter on the BamHI-N fragment and the HSV-1 TK gene on the BamHI-Q fragment, fused at the BamHI/BglII sites, was ligated into the StuI site. The net result from this series of clonings was a plasmid which had suffered a deletion of 3kb from between the StuI sites, and into which 3.8kb of the foreign TK gene had been incorporated (see FIG. 2B). The TK gene was thus flanked by PRV DNA sequences to allow for insertion of the foreign gene into the PRV genome by homologous recombination. The plasmid DNA was tranfected into rabbit skin cells along with the intact PRV DNA from S-PRV-003, which is a pseudorabies virus that has a deletion in the endogenous TK gene. The transfection stock of virus was selected in HAT medium and the virus was identified and selected by analysis of the restriction pattern of DNA isolated from the infected cells.

S-PRV-004 contained the HSV-1 TK gene and was expressing this gene as demonstrated by the incorporation of 14C-thymidine in a plaque assay described in Tenser et al. (25) and by direct analysis of TK activity in infected cell extracts, following the procedure of Cheng et al. (26). The location of this gene in the genome of PRV is shown in FIG. 2C.

EXAMPLE 2

S-PRV-005

S-PRV-005 is a pseudorabies virus that has a deletion in the repeat region and in the endogenous PRV TK gene in the long unique region, and has an insertion of the HSV-1 TK gene under the control of the ICP4 promoter incorporated into both copies of the repeat region between the XbaI site and the HpaI site in the BamHI #5 fragment (See FIG. 3).

To create this virus, we first obtained a clone of BamHI #5 fragment from PRV (FIG. 1B). The BamHI #5 fragment was cloned into the plasmid pACYC184 at the BamHI site (see LIGATION above). A map of the BamHI #5 fragment is shown in FIG. 3A.

The plasmid containing the BamHI #5 fragment was cut with XbaI and HpaI and the linearized plasmid was purified (see PHENOL EXTRACTION OF DNA FROM AGAROSE). The 3.8kb PvuII fragment described in Example 1 and containing the TK gene and ICP4 promoter was likewise purified. The XbaI site was filled to yield a blunt end (see POLYMERASE FILL-IN REACTION), and the two DNAs were mixed and ligated together. The resulting plasmid that had incorporated the TK gene in the XbaI-HpaI deletion was selected and analyzed by restriction mapping (FIG. 3B).

The plasmid containing the TK gene flanked by PRV Bam HI #5 sequences was used to transfect rabbit skin cells along with purified DNA from S-PRV-003, a pseudorabies virus that had a deletion in the endogenous TK gene. The resulting recombinant PRV that had incorporated the HSV-1 TK gene into the deletion in the repeats was screened and purified from the transfection stock by the HYBRIDIZATION SCREEN FOR RECOMBINANT PRV procedure without any prior selection.

S-PRV-005 recombinant PRV was shown to express the HSV-1 TK gene by incorporation of $^{14}$C-thymidine in a plaque assay (25), by analysis of the TK activity in infected cell lysates (26), and by immunodetection of the HSV-1 TK protein according to the ANTIBODY SCREEN FOR RECOMBINANT PRV procedure outlined above. The location of this gene in the genome of PRV is shown in FIG. 3C.

EXAMPLE 3

S-PRV-010

S-PRV-010 is a pseudorabies virus that has a deletion in the PRV TK gene in the long unique region, a deletion in the repeat region, and the insertion of the *E. coli* B-galactosidase gene (lacZ gene) incorporated into both copies of the repeats at the XbaI site in BamHI #5 fragment (see FIG. 5A). The β-galactosidase gene was constructed to be expressed using the HSV-1 TK gene promoter which we have shown in this construct to be active in PRV.

The method used to insert the β-galactosidase gene into S-PRV-010 was direct ligation (see DIRECT LIGATION PROCEDURE FOR GENERATING RECOMBINANT PRV). The β-galactosidase gene was on plasmid pJF751, obtained from Jim Hoch, Scripps Clinic and Research Foundation. This gene is truncated at the 5'end with a BamHI site that has removed the AGT initiation codon, and the AvaI site in pBR322 was used at the other end (see FIG. 4A). The HSV-1 TK promoter (FIG. 4B) was taken from the McKnight TK gene as an RsaI fragment, gel purified, and ligated to a synthetic piece of DNA which contained a BamHI site within the sequence CGGATCCG (FIG. 4C). After digestion with BamHI, the fragment was cloned into the BamHI site at the start of the β-galactosidase gene (FIG. 4D). The plasmid was constructed with the *E.coli* plasmids pSP64 and pSP65 such that XbaI sites from the polylinkers could be used to excise the entire construct from the plasmid. The ligation mixture was used to transfect *E. coli* HB101 according to published procedures (Maniatis et al. (2)). This construct was planned such that the first three amino acids of the protein were from the HSV-1 TK gene, the next three were from the synthetic linker, and the rest were from the β-galactosidase gene. The gene contained the following sequence at the fusion between TK and lacZ:

```
5' CGT ATG GCT TCG TCG GAT CCC GTC GTT TTA . . . 3'
       MET ala ser ser asp pro val val leu . . .
   ----------------------       ------------------------------
       TK gene      -----------------------       lac Z
                         BamHI linker
```

A pseudorabies virus construct designated S-PRV-002 which has a deletion in the PRV TK gene in the unique long region and a deletion in the repeat region was used as the recipient for the β-galactosidase gene. Intact S-PRV-002 DNA was mixed with a 30-fold molar excess of plasmid DNA containing the β-galactosidase gene under the control of the HSV-1 TK promoter, and this mixture was digested with XbaI restriction enzyme. The ligated DNA was used to transfect animal cells, and the transfection stock was analyzed for recombinant PRV. First, PRV DNA was prepared from cells infected with the transfection stock virus and this DNA was cut with restriction enzymes and analyzed on an agarose gel. This analysis showed that the recombinant virus was present as the major species in the transfection stock, and it was subsequently purified from other virus species by plaque assay coupled with the BLUO-GAL SCREEN FOR RECOMBINANT PRV. Because β-galactosidase reacted with the drug Bluogal ® to yield a product with blue color, it was possible to plaque purify the recombinant by picking blue plaques.

The final result of the purification was the recombinant PRV designated S-PRV-010. It was shown to express the enzyme $\beta$-galactosidase by the formation of blue plaques as noted above, and by the detection of the enzyme in infected cell extracts using the substrate O-nitrophenyl-$\beta$-D-galactopyranoside (Sigma) following the procedure of Norton and Coffin (27). The location of this gene in the genome of PRV is shown in FIG. 5C.

Previous studies demonstrated that swine vaccinated with S-PRV-002 developed antibody to PRV and were fully protected against clinical disease following exposure to virulent PRV virus. Animal studies were conducted with S-PRV-010 to determine the utility of a recombinant pseudorabies virus as a vaccine against pseudorabies disease.

Weaned pigs (4–6 weeks old) that had no prior exposure to PRV and 4-day-old piglets born from a sow with no prior exposure to PRV were inoculated with $10^{4.0}$ or $10^{6.0}$ $TCID_{50}$ of S-PRV-010 virus. The animals were observed daily for 14 days to detect clinical signs of PRV and body temperatures were recorded daily. At designated times, blood samples were taken from the pigs and the serum was tested for antibody to PRV, using a radioimmunodiffusion enzyme-linked immunosorbent assay (RIDEA). Approximately 3 weeks after vaccination, the vaccinated pigs, along with non-vaccinated control pigs, were challenged by intranasal adminstration of $10^{3.0}$ $TCID_{50}$ of virulent virus. The challenged animals wer observed 14 days for signs of PRV.

The $LD_{50}$ of this virus in mice was greater than $10^{6.0}$ (data not shown). Responses of weaned pigs vaccinated with S-PRV-010 are shown in Table 1. Administration of this virus did not cause adverse reactions in the pigs. The vaccinated animals developed PRV neutralizing antibody. Two, non-vaccinated control animals (#75 and #91) placed in contact with the vaccinates did not develop PRV antibody prior to challenge, indicating the vaccine virus was not shed from vaccinates. After challenge, all ten vaccinated animals remained clinically normal and free of PRV disease. In contrast, the two in-contact control animals and three of five non-vaccinated control animals developed PRV.disease and one of these pigs died of PRV.

To test further the utility of S-PRV-010 as a vaccine, the virus was inoculated into 4-day old piglets. The results, presented in Table 2, demonstrated that the elicited an antibody response in vaccinated piglets and did not cause adverse reactions. The virus apparently was shed from vaccinates, since one (#67) of two non-vaccinated, in-contact control piglets had developed PRV antibody by Day 24. After challenge, all vaccinated animals and the sero-positive in-contact control animal remained free of PRV disease. By comparison, the three non-vaccinated control pigs and the second in-contact control pig developed clinical signs of PRV and died.

The conclusion from that study is that S-PRV-010 given at a dosage of $10^{4.0}$ or $10^{6.0,}$ elicits a protective response in vaccinated piglets or weaned pigs capable of preventing infection by virulent virus.

TABLE I

SEROLOGIC AND CLINICAL RESPONSES OF WEANED PIGS FOLLOWING VACCINATION WITH S-PRV-010 AND CHALLENGE WITH WILD-TYPE PRV

| | | Antibody Titers[a] | | | | | |
|---|---|---|---|---|---|---|---|
| | | Post-Vaccination | | | Post-Challenge | | Post-Challenge Clinical |
| Vaccine GROUP | Pig Number | Day 0 | Day 14 | Day 24 | Day 7 | Day 14 | Signs |
| $10^{6.0}$ | 70 | <2 | 64 | 32 | 32 | 64 | None |
| Per | 71 | <2 | 16 | 16 | 16 | 32 | None |
| Dose | 72 | <2 | 64 | 32 | 16 | 64 | None |
| | 73 | <2 | 64 | 16 | 16 | 64 | None |
| | 74 | <2 | 16 | 8 | 4 | 4 | None |
| | 75[b] | <2 | <2 | <2 | <2 | 4 | Depressed, Dyspnea, CNS Signs[c] |
| $10^{4.0}$ | 76 | <2 | 64 | 4 | 8 | 32 | None |
| Per | 77 | <2 | 16 | 16 | 64 | 8 | None |
| Dose | 78 | <2 | 32 | 16 | 32 | 8 | None |
| | 79 | <2 | 8 | 16 | 64 | 4 | None |
| | 80 | <2 | <2 | <2 | 256 | 16 | None |
| | 81[b] | <2 | <2 | <2 | <2 | 16 | Depressed Rhinitis, CNS Signs |
| Controls | 82 | NT | NT | <2 | <2 | 8 | None |
| | 83 | NT | NT | <2 | <2 | 16 | None |
| | 84 | NT | NT | <2 | <2 | 32 | CNS Signs, Depressed, Dyspnea |
| | 85 | NT | NT | <2 | <2 | 64 | CNS Signs |
| | 86 | NT | NT | <2 | <2 | — | CNS Signs, Died |

[a]Determined by RIDEA
[b]In-contact Controls
[c]CNS signs include Ataxia, Incoordination, Circling, Lateral Recumbency
NT: Not Tested

TABLE II

SEROLOGIC AND CLINICAL RESPONSES OF 4-DAY-OLD PIGLETS FOLLOWING VACCINATION WITH S-PRV-010 AND CHALLENGE WITH WILD-TYPE PRV

| Vaccine GROUP | Pig Number | Antibody Titers[a] | | | | | Post-Challenge Clinical Signs |
|---|---|---|---|---|---|---|---|
| | | Post-Vaccination | | | Post-Challenge | | |
| | | Day 0 | Day 14 | Day 24 | Day 7 | Day 14 | |
| $10^{6.0}$ | 60 | <2 | 4 | 16 | 16 | 32 | None |
| Per | 61 | <2 | 64 | 8 | 64 | 8 | None |
| Dose | 62 | <2 | 32 | 2 | 16 | 16 | None |
| $10^{4.0}$ | 63 | <2 | —[b] | — | — | — | — |
| Per | 64 | <2 | 64 | 2 | 32 | 16 | None |
| Dose | 65 | <2 | 2 | 4 | 32 | 16 | None |
| In- | 66 | <2 | 2 | NT | —[c] | — | Comatose, Died |
| Contact Controls | 67 | <2 | <2 | 8 | 64 | 32 | None |
| Controls | 87 | NT | NT | <2 | —[c] | — | CNS Signs[d], Died |
| | 88 | NT | NT | <2 | —[c] | — | CNS Signs, Died |
| | 89 | NT | NT | <2 | —[c] | — | Died |

[a] Determined by RIDEA
[b] Died 8 Days Post Vaccination From Ruptured Stomach
[c] Died on or Prior to Day 7 Post-Challenge
[d] CNS Signs include Ataxia, Incoordination, Circling Lateral Recumbency
NT: Not Tested

EXAMPLE 4

S-PRV-007

S-PRV-007 is a pseudorabies virus that has a deletion in the PRV TK gene in the unique long region, a deletion in the repeat region, and the swine rotavirus glycoprotein 38 gene under the control of the HSV-1 ICP4 promoter inserted into the repeat region.

S-PRV-005 virus described in Example 2 above was further engineered to contain the rotavirus antigen (see FIG. 6) as follows. The swine rotavirus gp38 gene was cloned into plasmid pBR322 at the PstI site by procedures previously described herein. The resulting plasmid was called pSY565 (see FIG. 7). The 1090 bp PstI fragment containing the gp38 gene was cloned into vector pUC4K at the PstI site such that it became flanked by BamHI sites in a plasmid called pSY762.

Plasmid pSY590 has had a complex origin as inferred from the flow chart. These clonings were routine in nature and are of historical interest but are not strictly required to practice the invention. Briefly this history is:

(1) The McKnight TK gene was the HSV-1 BamHI Q fragment from HaeIII at −178 relative to CAP site to BamHI at +2700 which was cloned between HindIII and BamHI in pBR327.

(2) pSY491...The entire TK coding region from the BglII site at +55 (relative to CAP site) to the BamHI site at +2700 was cloned into the BamHI site in pSP65 and called pSY491.

(3) pSY481...The polyA signal sequence (pA) on an 800 bp SmaI fragment from TK was subcloned into the SmaI site in pSP65 and was called pSY481.

(4) pSY583...The pA 800 bp SmaI fragment from pSY481 was cloned into the HincII site in pSP65 and called PSY583.

(5) pSY429...The HSV-1 BamHI N fragment was obtained from Dr. B. Roizman cloned into the BamHI site of pBR322 and was called pSY429.

(6) pSY584...The 2.2kb fragment of BamHI N from PvuII to BamHI (ref 5) in pSY420 was subcloned into pSP65 between HincII and BamHI in the polylinker and was called pSY584.

(7) pSY479...A plasmid was constructed from pSP64 and pSP65 that contained a fused polylinker sequence. Both plasmids were cut with PstI in the polylinker and PvuI in the plasmid body. The net effect of this construct was to create a fusion plasmid called pSP66 which has a symmetrical polylinker sequence centered on the PstI site. pSY479 is the name of this plasmid and it also contained a PstI fragment cloned into the PstI site that is irrelevant for the manipulations that follow.

Plasmid pSY590 was created from pSY583, pSY584, and pSY479 in a three fragment ligation of the following elements: the 3kb plasmid sequences from pSY479 (pSP66) cut with PstI, the 800 bp SmaI pA fragment cut from the polylinker in pSY583 with PstI and BamHI, and the 2200 bp BamHI N fragment cut from pSY583 with PstI and BamHI. FIG. 7 shows the final configuration of all of these DNA fragments in pSY590. There is a single BamHI site in the plasmid between the promoter in BamHI N and the TK pA signal that was used to insert the coding region of the gp38 gene.

For the creation of the homology vector used in the formation of S-PRV-007, the plasmid pSY590 was opened with BamHI, and the 1090 bp gp38 gene was removed from pSY762 by cutting with BamHI, and these two fragments were ligated together to form pSY596. The correct orientation of the gp38 gene was confirmed by diagnostic restriction enzyme digestion utilizing sites with gp38 (see FIG. 10).

In pSY596 described above, the gp38 gene resided between two flanking HSV-1 DNA fragments. These two regions were thus homologous to similar regions on the HSV-1 TK gene in S-PRV-005, and these regions were used for the homologous recombination to create S-PRV-007 (FIG. 6A). The plasmid and S-PRV-005 DNAs were mixed and used in the DNA TRANSFECTION PROCEDURE FOR GENERATING RECOMBINANT PRV. A virus that had incorporated the rotavirus antigen in place of the TK gene was selected with BUDR. Recombinants from the selected virus stock that had incorporated the rotavirus DNA were screened by the HYBRIDIZATION SCREEN FOR RECOMBINANT PRV and by analyzing restriction digests of DNA by the SOUTHERN BLOTTING OF DNA procedure using the rotavirus cloned gp38 gene as probe.

The final result of this screening was a recombinant PRV called S-PRV-007 which had the rotavirus gp38 gene incorporated into the repeat region between the XbaI and HpaI sites in PRV BamHI #5 fragment shown in FIG. 6C. The presence in a host of gp38 expressed by S-PRV-007 has not yet been detected.

EXAMPLE 5

S-PRV-012

S-PRV-012 is a pseudorabies virus that has a deletion in the PRV TK region in the unique long region, a deletion in the repeat region, and a deletion in the unique short region encoding the PRV glycoprotein X, called gpX and identified and mapped by Rea et al.(28). The HSV-1 TK gene under the control of the ICP4 promoter was inserted in place of the gpX gene.

The following procedure was used to make the deletion of gpX and the simultaneous insertion of the HSV-1 TK gene. The flanking regions for homology to PRV were from cloned fragments of BamHI #10 fragment and BamHI #7 fragment extending from NdeI to BamHI (FIG. 8). The BamHI and NdeI sites were filled in according to the POLYMERASE FILL-IN REACTION, and the PvuII fragment of HSV-1 DNA was inserted by LIGATION. This plasmid was transfected with intact S-PRV-002 DNA according to the DNA TRANSFECTION FOR GENERATING RECOMBINANT PRV procedure. The recombinant virus was selected by HAT SELECTION OF RECOMBINANT PRV procedure, and screened by the ANTIBODY SCREEN FOR RECOMBINANT PRV procedure using antibodies specific for the HSV-1 protein.

The recombinant virus selected by this procedure was designated S-PRV-012 and has been deposited with the ATCC under Accession No. VR-2119 and was shown by RESTRICTION MAPPING OF DNA and SOUTHERN BLOTTING OF DNA to contain the HSV-1 TK gene inserted in place of the PRV gpX gene (FIG. 8B). The ANTIBODY SCREEN FOR RECOMBINANT PRV procedure showed that the virus was expressing the inserted HSV-1 TK gene. The structure of this virus is shown in FIG. 8C.

EXAMPLE 6

S-PRV-013

S-PRV-013 is a pseudorabies virus that has a deletion in the PRV TK gene in the long unique region, a deletion in the repeat region, and a deletion in the gpX coding region. The gene for *E. coli* β-galactosidase was inserted in place of the gpX gene and is under the control of the endogenous gpX gene promoter.

The following procedures were used to create S-PRV-013 by homologous recombination. The flanking PRV homology regions were from cloned BamHI #10 fragment which contains the gpX promoter, and from cloned BamHI #7 fragment ment extending from the NdeI site to the BamHI site (FIG. 9A). The NdeI site was filled in according to the POLYMERASE FILL-IN REACTION, and the β-galactosidase gene was inserted between the BamHI #10 and BamHI #7 fragments. This construct positioned the β-gal gene behind the gpX promoter and the gpX poly A signal sequence with a deletion of almost all of the coding region of gpX. The plasmid DNA and DNA from S-PRV-002 were mixed and transfected according to the DNA TRANSFECTION FOR GENERATING RECOMBINANT PRV procedure. The recombinant virus was screened and purified from the transfection stock by the BLUOGAL SCREEN FOR RECOMBINANT PRV procedure.

The resulting virus from this screen was called S-PRV-013 and has been deposited with the ATCC under Accession NO. VR 2120. It contained the β-galactosidase gene in place of the gpX coding region (FIGS. 9B and 9C) as determined by PREPARATION OF PRV DNA followed by SOUTHERN BLOTTING OF DNA. The expression of the β-galactosidase gene was confirmed by the BLUOGAL SCREEN FOR RECOMBINANT PRV test, and by the o-nitrophenylgalactopyranoside substrate assay (27).

1. S.B. Mohanty and S.K. Dutta, Veterinary Virology, Lea and Febiger Publishers, Philadelphia, 1981.
2. Maniatis et al., Molecular Cloning: A Laboratory Manual, Cold Spring Harbor Laboratory Press, 1982.
3. D.M. Knipe et al., Proceedings of the National Academy of Sciences U.S.A. 75, 3896–3900, 1978.
4. E.S. Mocarski et al., Cell 22, 243–244, 1980.
5. L.E. Post et al., Cell 24, 555–565, 1981.
6. L.E. Post and B. Roizman, Cell 25, 227–232, 1981.
7. K.L. Poffenberger et al., Proceedings of the National Academy of Sciences U.S.A. 80, 2690–2694, 1981.
8. M.G. Gibson and P.G. Spear, Journal of Virology 48, 396–404, 1983.
9. G.T.-Y. Lee et al., Proceedings of the National Academy of Sciences U.S.A. 79, 6612–6616, 1982.
10. M.-F. Shih et al., Proceedings of the National Academy of Sciences U.S.A. 81, 5867–5870, 1984.
11. R. Desrosiers et al., Ninth Annual Herpesvirus Meeting, Seattle, Abstract #280, 1984.
12. B. Roizman et al., Intervirology 16, 201–217, 1981.
13. S. Ihara et al., Virology 122, 268–278, 1982.
14. B. Lomniczi et al., Journal of Virology 49, 970–979, 1984.
15. S. Kit et al., Ninth International Herpesvirus Workshop, Seattle, Abstract #216 (1984).
16. A. Berns et al., Journal of Virology 53, 89–93, 1985.
17. A.L.J. Gielkens et al., Journal of General Virology 66, 69–82, 1985.
18. M. Arsenakis and B. Roizman, in "The High Technology Route to Virus Vaccines", American Society for Microbiology, Washington, D.C., 1985 (Proceedings of the First Annual Southwest Foundation for Biomedical Research International Symposium, Houston, TX, 8–10 November, 1984).
19. S. Kit et al., in "The High Technology Route to Virus Vaccines", American Society for Microbiology, Washington, D.C., 1985 (Proceedings of the First Annual Southwest Foundation for Biomedical Research International Symposium, Houston, TX, 8–10, November, 1984).
20. L.E. Post et al., Tenth International Herpesvirus Workshop, Ann Arbor, August, 1985.
21. F. Graham and A. Van der Eb, Virology 52, 456–467, 1973.
22. J. Campione Piccardo et al., J. Virology 31, 28114 287, 1979.
23. L Villarreal and P. Berg, Science 196, 183–185, 1977.
24. M.A. Richardson et al., J. Virology 51, 860, 1985.
25. R.B. Tenser et al., J. Clinical Microbiol. 17, 122–127, 1983.
26. Y-C.Cheng et al., J. Virological Methods 5, 209–217, 1982.

27. P.A. Norton and J.M. Coffin, Molecular and Cellular Biology 5, 281-290, 1985.

28. T.J. Rea et al., J. of Virology 54, 21-29, 1985.

What is claimed is:

1. A non-naturally occurring, attenuated pseudorabies virus designated S-PRV-014 (ATCC Accession No. VR 2120).

* * * * *

UNITED STATES PATENT AND TRADEMARK OFFICE
CERTIFICATE OF CORRECTION

PATENT NO. : 5,068,192

DATED : November 26, 1991

INVENTOR(S) : Mark D. Cochran

It is certified that error appears in the above-identified patent and that said Letters Patent is hereby corrected as shown below:

On column 4, line 56, "S-PRV005"
should read --S-PRV-005--.

On column 5, line 13, "Ba = BamHI"
should read --B = BamHI--.

On column 6, line 21, "pseudorabie"
should read --pseudorabies--.

On column 7, lines 43-44 "natural-lyoccurring"
should read --naturally-occurring--.

On column 9, line 13, "31 70°C"
should read -- -70°C--.

On column 10, line 18, "Betheada"
should read --Bethesda--.

On column 10, line 31, "40-14 50V"
should read --40-50V--.

On column 14, line 9 delete the first "the".

On column 16, line 61, "hte"
should read --the--.

On column 17, line 22, "14C"
should read --$^{14}$C--.

On column 20, line 3, "wer"
should read --were--.

UNITED STATES PATENT AND TRADEMARK OFFICE
CERTIFICATE OF CORRECTION

PATENT NO. : 5,068,192

DATED : November 26, 1991

INVENTOR(S) : Mark D. Cochran

It is certified that error appears in the above-identified patent and that said Letters Patent is hereby corrected as shown below:

On column 20, line 22, before "elicited" insert --virus--.

On column 23, line 56, delete "ment".

On column 24, line 13, insert the heading --REFERENCES--.

On column 24, lines 60-61, "28114 287" should read --281-287--.

In claim 1, line 2, "S-PRV-014" should read --S-PRV--013--.

Signed and Sealed this

Twenty-seventh Day of April, 1993

*Attest:*

*Attesting Officer*

MICHAEL K. KIRK

*Acting Commissioner of Patents and Trademarks*